United States Patent
Burke et al.

(10) Patent No.: US 6,514,533 B1
(45) Date of Patent: *Feb. 4, 2003

(54) DEVICE FOR THE SUSTAINED RELEASE OF AGGREGATION-STABILIZED, BIOLOGICALLY ACTIVE AGENT

(75) Inventors: Paul A. Burke, Oxnard, CA (US); Stephen E. Zale, Hopkinton, MA (US); Mark A. Tracy, Arlington, MA (US); OluFunmi Lily Johnson, Cambridge, MA (US); Howard Bernstein, Cambridge, MA (US); M. Amin Khan, Dowington, PA (US); Henry E. Auer, Chicago, IL (US)

(73) Assignee: Alkermas Controlled Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/934,830
(22) Filed: Sep. 22, 1997

Related U.S. Application Data

(63) Continuation of application No. 08/521,744, filed on Aug. 31, 1995, now abandoned, which is a continuation-in-part of application No. 08/765,558, filed as application No. PCT/US95/07348 on Jun. 7, 1995, which is a continuation-in-part of application No. 08/279,784, filed on Jul. 24, 1994, now Pat. No. 5,711,968, application No. 08/934,830, which is a continuation-in-part of application No. 08/478,502, filed on Jun. 7, 1995, now Pat. No. 5,716,644, which is a continuation-in-part of application No. 07/885,307, filed on Jun. 11, 1992, now abandoned, application No. 08/934,830, which is a continuation-in-part of application No. 08/483,318, filed on Jun. 7, 1995, now Pat. No. 5,674,534, which is a continuation-in-part of application No. 07/885,307, application No. 08/934,830, which is a continuation-in-part of application No. 08/473,544, filed on Jun. 7, 1995, now Pat. No. 5,654,010, which is a continuation-in-part of application No. 07/984,323, filed on Dec. 2, 1992, now abandoned, application No. 08/934,830, which is a continuation-in-part of application No. 08/477,725, filed on Jun. 7, 1995, now Pat. No. 5,667,808, which is a continuation-in-part of application No. 07/984,323.

(51) Int. Cl.$^7$ .............. A61K 9/10; A61K 9/22; A61K 9/52; A61K 47/34; A61K 47/02
(52) U.S. Cl. .......... 424/486; 424/468; 424/457; 514/970
(58) Field of Search .............. 424/486, 426, 424/428, 468, 457; 514/970

(56) References Cited

U.S. PATENT DOCUMENTS

| 3,887,699 A | 6/1975 | Yolles .................. 424/19 |
| 3,891,570 A | 6/1975 | Fukushima et al. ......... 252/316 |

(List continued on next page.)

FOREIGN PATENT DOCUMENTS

| EP | 0266119 A3 | 10/1987 |
| WO | WO 90/13285 | 11/1990 |

(List continued on next page.)

OTHER PUBLICATIONS

Santo, Toyomi et al., "Porous Biodegradable Microspheres for Controlled Drug Delivery. I. Assessment of Processing Conditions and Solvent Removal Techniques," *Pharmaceutical Research*, 5(1):21–29 (1988).

Langer, R., "New Methods of Drug Delivery," *Science*, 249:1527–1533 (Sep. 28, 1990).

(List continued on next page.)

Primary Examiner—Edward J. Webman
(74) Attorney, Agent, or Firm—Hamilton, Brook, Smith & Reynolds, P.C.

(57) ABSTRACT

A device for the sustained release in vivo of a water soluble, biologically active agent wherein the agent is susceptible to aggregation comprising a drug delivery device and aggregation-stabilized, biologically active agent wherein the aggregation-stabilized agent is disposed within the drug delivery device.

8 Claims, 21 Drawing Sheets

U.S. PATENT DOCUMENTS

| | | | |
|---|---|---|---|
| 4,235,236 A | 11/1980 | Theeuwes | 128/260 |
| 4,252,791 A | 2/1981 | Grossberg et al. | 424/85 |
| 4,391,797 A | 7/1983 | Folkman et al. | 424/19 |
| 4,530,840 A | 7/1985 | Tice et al. | 514/179 |
| 4,542,025 A | 9/1985 | Tice et al. | 424/78 |
| 4,637,905 A | 1/1987 | Gardner | 264/4.3 |
| 4,675,189 A | 6/1987 | Kent et al. | 424/490 |
| 4,835,139 A | 5/1989 | Tice et al. | 514/15 |
| 4,853,218 A | 8/1989 | Yim et al. | 424/85.7 |
| 4,897,268 A | 1/1990 | Tice et al. | 424/422 |
| 4,962,091 A | 10/1990 | Eppstein et al. | 514/2 |
| 5,019,400 A | 5/1991 | Gombotz et al. | 424/497 |
| 5,126,147 A | 6/1992 | Silvestri et al. | 424/497 |
| 5,192,741 A | 3/1993 | Orsolini et al. | 514/4 |
| 5,441,734 A | 8/1995 | Reichert et al. | 424/85.7 |
| 5,697,922 A * | 12/1997 | Thombre | |
| 6,087,324 A | 7/2000 | Igari et al. | 514/2 |
| 6,376,461 B1 | 4/2002 | Igari et al. | 514/2 |

FOREIGN PATENT DOCUMENTS

| | | |
|---|---|---|
| WO | WO 90/13780 | 11/1990 |
| WO | WO 92/11844 | 7/1992 |
| WO | WO 91/12882 | 9/1992 |
| WO | WO 93/17668 | 9/1993 |
| WO | WO 93/25221 | 12/1993 |
| WO | WO 94/12158 | 6/1994 |
| WO | WO 95/11010 | 4/1995 |
| WO | WO 95/29664 A1 | 11/1995 |
| WO | WO 96/07399 A1 | 3/1996 |

OTHER PUBLICATIONS

Liu, W.R. et al., "Moisture–Induced Aggregation of Lyophilized Proteins in the Solid State," *Biotechnology and Bioengineering*, 37:177–184 (1991).

Lu, W. and Park, T.G., "Protein Release from Poly(lactic-co-glycolic acid) Microspheres: Protein Stability Problems," *PDA Journal of Pharmaceutical Science & Technology*, 49(1):13–19 (Jan.–Feb. 1995).

Cohen, S. et al., "Controlled Delivery Systems for Proteins Based on Poly(Lactic/Glycolic Acid) Microspheres," *Pharmaceutical Research*, 8(6):713–720 (1991).

Hora, M.S. et al., "Release of Human Serum Albumin from Poly(latide–co–glycolide) Microspheres," *Pharmaceutical Research*, 7(11):1190–1194 (1990).

Hageman, M.J. et al., "Preformulation Studies Oriented Toward Sustained Delivery of Recombinant Somatotropins," *J. Agric. Food Chem.*, 40:348–355 (1992).

Cleland, J.L. et al., "Characterization of Recombinant Human Growth Hormone–PLGA Formulations in Animals," *Proceed, Intern. Symp. Control. Rel. Bioact. Mater.*, 22:143–144 (1995).

Park, T.G. et al., "Importance of In Vitro Experimental Conditions on Protein Release Kinetics, Stability and Polymer Degradation in Protein Encasulated Poly(D,L–Lactic Acid–Co–Glycolic Acid) Microspheres," *Journal of Controlled Release*, 33:211–222 (1995).

* cited by examiner

DEVICE FOR THE SUSTAINED RELEASE OF AGGREGATION-STABILIZED, BIOLOGICALLY ACTIVE AGENT

RELATED APPLICATIONS

This application is a Continuation of U.S. patent application Ser. No. 8/521,744, filed Aug. 31, 1995, now abandoned, which is Continuation-in-Part U.S. patent application Ser. No. 08/765,558, which is the U.S. National Phase of PCT Application PCT/US95/07348, filed Jun. 7, 1995, which is a Continuation-in-Part of U.S. Ser. No. 08/279,784, filed Jul. 24, 1994, now U.S. Pat. No. 5,711,968. This application is also a Continuation-in-Part of U.S. patent application Ser. No. 08/478,502, filed Jun. 7, 1995, now U.S. Pat. No. 5,716,644, which is a Continuation in-Part of U.S. patent application Ser. No. 07/885,307, filed Jun. 11, 1992, now abandoned; U.S. patent application Ser. No. 08/483,318, filed Jun. 7, 1995, now U.S. Pat. No. 5,674,534, which is a Continuation-in-Part of U.S. patent application Ser. No. 07/885,307, filed Jun. 11, 1992, now abandoned; U.S. Pat. No. 08/473,544, filed Jun. 7, 1995, now U.S. Pat. No. 5,654,010, which is a Continuation-in-Part of U.S. application Ser. No. 07/984,323, filed Dec. 2, 1992, now abandoned; and U.S. application Ser. No. 08/477,725, filed Jun. 7, 1995, now U.S. Pat. No. 5,667,808, which is a Continuation-in-Part of U.S. application Ser. No. 07/984,323, filed Dec. 2, 1992, now abandoned. The entire teachings of all of the above listed documents are incorporated herein by reference.

BACKGROUND OF THE INVENTION

Many illnesses or conditions require administration of a constant or sustained level of a medicament or biologically active agent to provide the most effective prophylactic or therapeutic. This may be accomplished through a multiple dosing regimen or by employing a system that releases the medicament in a sustained fashion.

Attempts to sustain medication levels include the use of biodegradable materials, such as polymeric matrices, containing the medicament. The use of these matrices, for example, in the form of microparticles or microcarriers, provides an improvement in the sustained release of medicaments by utilizing the inherent biodegradability of the polymer to control the release of the medicament and provide a more consistent, sustained level of medication and improved patient compliance.

However, these sustained release devices often exhibited high initial bursts of agent release and minimal agent release thereafter. Further, due to the high solution concentration of agent within and localized around these sustained release devices, the agent molecules have tended to aggregate thereby increasing immunogenicity in vivo and interfering with the desired release profile for the agent.

Therefore, a need exists for a means for sustaining the release of a biologically active agent in vivo without significant aggregate formation and thus with a reduced immune response to the agent over the release period of the agent.

SUMMARY OF THE INVENTION

This invention relates to a device for the sustained release in vivo of a water soluble, biologically active agent wherein said agent is susceptible to aggregation, comprising a drug delivery device and aggregation-stabilized, biologically active agent wherein the aggregation-stabilized agent is disposed within the drug delivery device.

There are many advantages to this sustained release device for a biologically active agent. These advantages include longer, more consistent in vivo blood levels of the agent, lower initial bursts of the agent, and increased therapeutic benefits by eliminating fluctuations in serum agent levels. The advantages also include better retention of biological activity of the agent and reduced immunogenicity when in vivo. The advantages further include more complete release of an agent from a sustained release device.

BRIEF DESCRIPTION OF THE DRAWINGS

FIG. 1 is a plot of a) the cumulative release of monomeric erythropoietin (EPO), b) the cumulative release of EPO (monomer EPO plus aggregated EPO), and c) the percentage of EPO which is released as a monomer during the interval between an indicated time point and the immediately preceding time point, in vitro in HEPES buffer, from microcarriers of unblocked poly(lactide-co-glycolide) polymer (PLGA) (10,000 Dalton MW), containing 10% (w/w) $MgCO_3$ and 5% (w/w) of the Am1 formulation of Example 6, versus time over a 28 day interval.

FIG. 2 is a plot of a) the cumulative release of monomeric EPO, b) the cumulative release of EPO (monomer plus aggregate), and c) the percentage of EPO which is released as a monomer, during the interval between an indicated time point and the immediately preceding time point in vitro in HEPES buffer, from microcarriers unblocked PLGA (10,000 Dalton MW), containing 10% (w/w) $MgCO_3$ and 5% (w/w) of the Am7 formulation of Example 6, versus time over a 28 day interval.

FIG. 3 is a plot of a) the cumulative release of monomeric EPO, b) the cumulative release of EPO (monomer plus aggregate), and c) the percentage of EPO which is released as a monomer, during the interval between an indicated time point and the immediately preceding time point in vitro in HEPES buffer, from microcarriers of blocked PLGA (10,000 Dalton MW), containing 10% (w/w) $ZnCO_3$ and 10% (w/w) of the Zn1 formulation of Example 6, versus time over a 28 day interval.

FIG. 4 is a plot of the serum concentration (IU/ml) of Interferon-α,2b (IFN-α,2b) in rats, which were subcutaneously administered IFN-α,2b controlled release formulated microcarriers of Example 2, versus time over a 6 day interval.

FIG. 5 is a plot of the serum concentration (IU/ml) of IFN-α,2b in rats, which were subcutaneously administered IFN-α,2b controlled release Formula 2 microcarriers of Example 2, versus time over a 6 day interval.

FIG. 6 is a plot of the serum concentration (IU/ml) of IFN-α,2b in rats, which were subcutaneously administered IFN-α,2b controlled release Formula 3 microcarriers of Example 2, versus time over a 7 day interval.

FIG. 7 is a plot of the serum concentration (IU/ml) of IFN-α,2b in rats, which were subcutaneously administered IFN-α,2b controlled release Formula 4 microcarriers of Example 2, versus time over a 7 day interval.

FIG. 8 is a plot of the serum concentration (IU/ml) of IFN-α,2b, in rats, which were subcutaneously administered IFN-α,2b controlled release Formula 5 microcarriers of Example 2, versus time over a 7 day interval.

FIG. 9 is a plot of the serum concentration (IU/ml) of IFN-α,2b in rats, which were subcutaneously administered IFN-α,2b controlled release Formula 6 microcarriers of Example 2, versus time over a 7 day interval.

FIG. 10 is a plot of the serum concentration (IU/ml) of IFN-α,2b versus time over a 7 day interval in rats which were subcutaneously administered IFN-α,2b controlled release Formula 7 microcarriers of Example 2 having a 1:1 zinc carbonate-to-IFN-α,2b ratio.

FIG. 11 is a plot of the serum concentration (IU/ml) of IFN-α,2b versus time over a 29 day interval in rats which were subcutaneously administered a) IFN-α,2b controlled release microcarriers of Formula 8 of Example 2, wherein the rats were immunosuppressed with cyclosporin A and hydrocortisone (two groups) and b) the same formulation of IFN-α,2b controlled release microcarriers wherein the rats were not immunosuppressed.

DETAILED DESCRIPTION OF THE INVENTION

Figure 1:
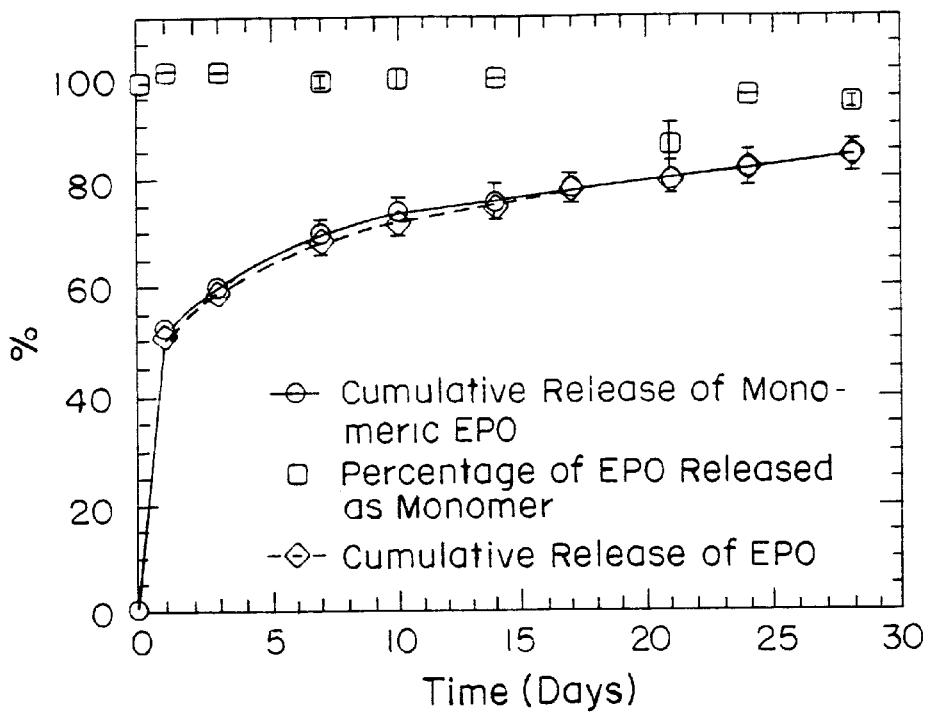

A biologically active agent, as defined herein, is an agent, or its pharmaceutically acceptable salt, which is in its molecular, biologically active form when released in vivo, thereby possessing the desired therapeutic and/or prophylactic properties in vivo. Biologically active agents suitable for the composition and method of the invention are agents which are soluble in aqueous solutions and biological fluids and which are susceptible to aggregation in vivo. Examples of suitable biologically active agents include proteins such as immunoglobulin-like proteins, antibodies, cytokines (e.g., lymphokines, monokines, chemokines), interleukins, interferons, erythropoietin, nucleases, tumor necrosis factor, colony stimulating factors, insulin, enzymes, tumor suppressors, hormones (e.g., growth hormone and adrenocorticotropic hormone), antigens (e.g., bacterial and viral antigens) and growth factors; peptides such as protein inhibitors; nucleic acids, such as antisense molecules; oligonucleotides; and ribozymes.

A sustained release of a biologically active agent is a release which results in biologically effective serum levels of the biologically active, molecular (monomeric or non-aggregated) form of the agent over a period longer than that obtained following direct administration of an aqueous solution of the agent. A biologically effective serum level of an agent is a level which will result in the desired biological response within the recipient. Usually, in a sustained release, the serum level of the agent is above endogenous levels. Typically, a sustained release of an agent is for a period of a week or more, and preferably for two weeks or more.

A sustained release of non-aggregated, biologically active agent can be a continuous or non-continuous release with relatively constant or varying rates of release from a drug delivery device. The continuity of release of the biologically active agent can be affected by the loading of the agent, selection of excipients to produce the desired effect, and/or by other conditions such as the type of polymer used if the biologically active agent is encapsulated within a polymeric matrix.

A drug delivery device, as defined herein, includes any composition, such as diffusion-controlled polymeric and protein systems of the reservoir or matrix-type, or systems such as pressure-driven osmotic or syringe pumps wherein the rate of release of a biologically active agent is sustained by use of a drug delivery device to release said agent in vivo.

Aggregation-stabilized biologically active agent, as defined herein comprises a suitable agent in its biologically active, molecular (monomeric) form wherein the biologically active agent is stabilized against aggregation during formation of the sustained release device and while the device is employed in vivo. A biologically active agent can be aggregation-stabilized by several means, such as by controlling the solubilization of the agent in vivo and by controlling the environmental conditions experienced by the agent during device formation and in vivo. These means are typically dependent upon the specific biologically active agent to be aggregation-stabilized. Preferably, the means for aggregation-stabilizing a biologically active agent should not convert the agent to a form that will reduce in vivo biological activity such as by oxidation.

An aggregation-stabilized biologically active agent is stabilized against significant aggregation in vivo over the sustained release period. Significant aggregation is defined as an amount of aggregation that will reduce or preclude the achievement of effective serum levels in vivo of the biologically active agent over the sustained release period. Typically, significant aggregation is aggregation of about 10% or more of the original amount of biologically active agent in the sustained drug delivery device. Preferably, aggregation is maintained below about 5% of the initial loading of the molecular form of the agent. More preferably, aggregation is maintained below about 2% of the initial loading of biologically active agent.

In one embodiment of the sustained release device of the present invention, the biologically active agent is mixed with an aggregation-stabilizer wherein the in vivo solubilization of the biologically active agent is controlled. Typically an aggregation-stabilizer reduces the solubility of the biologically active agent, precipitates out a salt of the agent or forms a complex of the agent. The aggregation-stabilizer and the biologically active agent can be separately contained within the sustained drug delivery device, such as a device containing particles of aggregation-stabilizer and separate particles of biologically active agent, and/or can be combined together in complexes or particles which contain both the aggregation-stabilizer and the biologically active agent.

The suitability of candidate aggregation-stabilizers for stabilizing a biologically active agent against aggregation can be determined by one of ordinary skill in the art by performing a variety of stability indicating techniques such as SEC, polyacrylamide gel electrophoresis (PAGE) and potency tests on protein obtained from particles containing the aggregation-stabilized agent and for the duration of release from the sustained release device, as described in Example 5 for hGH and Examples 8–9 for EPO.

Suitable particles of aggregation-stabilized biologically active agent are solid particles, including lyophilized particles, freeze-dried particles, pressed pellets, and particles formed by any other means known in the art for forming a solid particle from a mixture of two components (e.g., biologically active agent and an aggregation stabilizer) wherein one component is temperature sensitive.

The amount of an agent which is contained in a sustained release device containing biologically active, aggregation-stabilized particles of the agent is a therapeutically or prophylactically effective amount which can be determined by a person of ordinary skill in the art taking into consideration factors such as body weight, condition to be treated, type of device used, and release rate from the device.

In one example of this embodiment wherein the in vivo solubilization of a biologically active agent is controlled, a biologically active agent is aggregation-stabilized when mixed with at least one type of metal cation from a metal cation component, which is the aggregation-stabilizer, wherein the agent is complexed and/or complexes in vivo with the metal cation to aggregation-stabilize the agent.

Suitable aggregation-stabilizing metal cations include biocompatible metal cations which will not significantly oxidize the agent. Typically, oxidation of a biologically active agent by a metal cation is not significant if this oxidation results in a loss of the agent's potency of about 10% or less. A metal cation component is biocompatible if it is non-toxic to the recipient in the quantities used, and also presents no significant deleterious or untoward effects on the recipient's body, such as an immunological reaction at the injection site. Preferably, the metal cation is multivalent.

Examples of suitable aggregation-stabilizing metal cations include cations of non-transition metals, such as $Mg^{+2}$ and $Ca^{+2}$. Suitable aggregation-stabilizing metal cations also include cations of transition metals, such as $Cu^{+2}$, $Co^{+2}$, $Fe^{+3}$ and $Ni^{+2}$. In a preferred embodiment, $Zn^{+2}$ is used as an aggregation-stabilizing metal cation. The suitability of metal cations for stabilizing a biologically active agent can be determined by one of ordinary skill in the art by performing a variety of stability indicating techniques such as polyacrylamide gel electrophoresis, isoelectric focusing, reverse phase chromatography, size exclusion chromatography (SEC) and potency tests on particles of the biologically active agent containing metal cations to determine the potency of the agent after particle formation, such as by lyophilization, and for the duration of release from microparticles.

It is preferred that the metal cation and biologically active agent are complexed within the sustained drug delivery device before administration to a subject.

It is also preferred that the mixture of the metal cation and the biologically active agent are in the form of solid particles, more preferably, lyophilized particles.

The molar ratio of metal cation to biologically active agent is typically between about 1:2 and about 100:1, and is preferentially between about 2:1 and about 10:1.

The use of metal cations to form aggregation-stabilized particles of the biologically active agents, interferon (IFN) and human growth hormone (hGH), are further described in Examples 1 and 4. In addition, the formation of sustained release devices of polymeric microcarriers containing metal cation-stabilized IFN or hGH are described in Examples 2 and 5. Furthermore, the aggregation-stabilization efficacy of metal cations complexed with IFN or hGH, within lyophilized particles dispersed in polymeric microcarriers, over a sustained release period in viva are described in Examples 10–12 or Examples 13–16, respectively.

The use of additional metal cations, dispersed within the polymeric matrix of a sustained release device, to further aggregation-stabilize a biologically active agent (hGH or IFN) are described in Examples 14 and 18.

The polymeric matrix is believed to function as a reservoir of metal cations so that the formation of cation-complexed protein is favored and dissociation into soluble protein is disfavored. Wherein the aqueous solubility of the metal cation component in the polymeric matrix is low, the release of metal cations from the matrix is slow, thus modulating the solubility of the protein.

In another example of the embodiment wherein the solubility of a biologically active agent is reduced by an aggregation stabilizer, the biologically active agent is mixed with an aggregation stabilizer which reduces solubility by precipitating the agent from the aqueous solution, thereby maintaining a suitably low localized concentration of soluble agent below a concentration at which significant aggregation occurs. A localized concentration of an agent is the concentration of solvated agent within, between or immediately surrounding the sustained release device. Suitable materials for precipitating an agent, such as a protein, without denaturing the agent, include salts which are in the Hofmeister series of precipitants of serum globulins (or "salting-out salts") as described by Thomas E. Creighton in *Proteins: Structures and Molecular Principles*, p149–150 (published by W. H. Freeman and Company, New York). Suitable salting-out salts for use in this invention include, for example, salts containing one or more of the cations $Mg^{+2}$, $Li^+$, $Na^+$, $K^+$ and $NH_4^+$; and also contain one or more of the anions $SO_4^{-2}$, $HPO_4^{-2}$, acetate, citrate, tartrate, $Cl^-$, $NO_3^-$, $ClO_3^-$, $I^-$, $ClO_4^-$ and $SCN^-$.

Again, the biologically active agent and the precipitant can be combined within particles and/or can be separately contained within the sustained release device. Preferably, a biologically active agent and a precipitant are combined in a lyophilized particle. The formation of lyophilized particles containing the agent erythropoietin and a precipitant, and the use of these particles in polymeric microcarrier sustained release devices, are described in Examples 6 and 7. The efficacy of precipitants in preventing aggregation of EPO in vitro and in vivo over a sustained period are also described in Examples 8–9 and Example 17, respectively.

In yet another embodiment for stabilizing a biologically active agent against aggregation, the agent is mixed with a buffer which will maintain the agent under pH conditions in vivo that can affect the rate of solubilization of the agent and/or prevent the formation in vivo of biologically inactive or insoluble forms (precipitates or gels which are insoluble in vivo) of the agent. Examples of such buffers include, for instance, phosphate buffers.

A preferred sustained release device of the present invention is a biocompatible polymeric matrix containing particles of an aggregation-stabilized biologically active agent dispersed therein. Polymers suitable to form a polymeric matrix of a sustained release device of this invention are biocompatible polymers which can be either biodegradable or non-biodegradable polymers, or blends or copolymers thereof.

A polymer, or polymeric matrix, is biocompatible if the polymer, and any degradation products of the polymer, are non-toxic to the recipient and also present no significant deleterious or untoward effects on the recipient's body, such as an immunological reaction at the injection site.

Biodegradable, as defined herein, means the composition will degrade or erode in vivo to form smaller chemical species. Degradation can result, for example, by enzymatic, chemical and/or physical processes. Suitable biocompatible, biodegradable polymers include, for example, poly(lactides), poly(glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetals, polycyanoacrylates, polyetheresters, poly(dioxanone)s, poly(alkylene alkylate)s, copolymers of polyethylene glycol and polyorthoester, biodegradable polyurethanes, blends and copolymers thereof.

Biocompatible, non-biodegradable polymers suitable for a sustained release device include non-biodegradable polymers selected from the group consisting of polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

Further, the terminal functionalities of a polymer can be modified. For example, polyesters can be blocked, unblocked or a blend of blocked and unblocked polyesters.

A blocked polyester is as classically defined in the art, specifically having blocked carboxyl end groups. Generally, the blocking group is derived from the initiator of the polymerization and is typically an alkyl group. An unblocked polyester is as classically defined in the art, specifically having free carboxyl end groups.

Acceptable molecular weights for polymers used in a sustained release device can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 5,000 Daltons to about 42,000 Daltons.

Typically, a polymeric sustained release microcarrier will contain from about 0.01% (w/w) to approximately 50% (w/w) of aggregation-stabilized biologically active agent (dry weight of the composition). The amount of agent used will vary depending upon the desired effect of the agent, the planned release levels, and the time span over which the agent will be released. A preferred range of agent loading is between about 0.1% (w/w) to about 30% (w/w) agent. A more preferred range of agent loading is between about 0.5% (w/w) to about 20% (w/w) agent.

In another embodiment, a polymeric sustained release composition also contains a biocompatible metal cation component, which is not contained in the biologically active, aggregation-stabilized particles, but is dispersed within the polymer. The metal cation of this metal cation component acts to modulate the release of the biologically active agent from the polymeric sustained release composition.

This metal cation component typically comprises at least one type of multivalent metal cations. A metal cation component, as defined herein, is a component containing at least one kind of multivalent metal cation (having a valency of +2 or more) in a non-dissociated state, a dissociated state, or a combination of non-dissociated and dissociated states. Suitable metal cation components include, for instance, metal salts, metal hydroxides, and basic (pH of about 7 or higher) salts of weak acids wherein the salt contains a metal cation. It is preferred that the metal cation be divalent. Examples of metal cation components suitable to modulate release of a biologically active agent, include, or contain, for instance, $Mg(OH)_2$, $MgCO_3$ (such as $4MgCO_3.Mg(OH)_2.5H_2O$), $ZnCO_3$ (such as $3Zn(OH)_2.2ZnCO_3$), $CaCO_3$, $Zn_3(C_6H_5O_7)_2$, $Mg(OAc)_2$, $MgSO_4$, $Zn(OAc)_2$, $ZnSO_4$, $ZnCl_2$, $MgCl_2$ and $Mg_3(C_6H_5O_7)_2$. A suitable ratio of metal cation component-to-polymer is between about 1:99 to about 1:2 by weight. The optimum ratio depends upon the polymer and the metal cation component utilized.

The metal cation component can optionally contain cation species and/or anion species which are contained in an aggregation stabilizer within particles of the agent. The metal cation component acts to modulate the release of the agent from the polymeric matrix of the sustained release composition and can also enhance the stability of agent in the composition against aggregation. In a modulated release, at least one release characteristic of the agent, such as the initial release level, the subsequent release levels, duration of release and/or the amount of agent released, is different from the release characteristics exhibited by the agent being released from a polymeric matrix, wherein the polymeric matrix does not contain a dispersed metal cation component.

A polymeric matrix containing a dispersed metal cation component to modulate the release of a biologically active agent from the polymeric matrix is further described in co-pending U.S. patent application Ser. No. 08/237,057, filed May 3, 1994 and co-pending PCT Patent Application PCT/US95/05511, the teachings of which are incorporated herein by reference in their entirety.

In yet another embodiment, at least one pore forming agent, such as a water soluble salt, sugar or amino acid, is included in a polymeric microparticle to modify the microstructure of the microparticle. The proportion of pore forming agent added to a polymer solution, from which the microparticle is formed, is between about 1% (w/w) to about 30% (w/w). It is preferred that at least one pore forming agent be included in a nonbiodegradable polymeric matrix.

The biologically active agent in a sustained release device of the present invention can also contain other excipients, such as stabilizers and bulking agents. Stabilizers are added to maintain the potency of the biologically active agent over the duration of the agent's release. Suitable stabilizers include, for example, carbohydrates, amino acids, fatty acids and surfactants and are known to those skilled in the art. For amino acids, fatty acids and carbohydrates, such as sucrose, lactose, mannitol, inulin, maltose, dextran and heparin, the mass ratio of carbohydrate to biologically active agent is typically between about 1:10 and about 20:1. For surfactants, such as polysorbates (e.g., Tween™) and polyoxamers and polyoxamines (e.g., Pluronic™), the mass ratio of surfactant to agent is typically between about 1:1000 and about 1:20.

Solubility agents can also be added to further modify the solubility of the agent. Suitable solubility agents include complexing agents, such as albumin and protamine, which can be used to slow the release rate of the agent from a polymeric matrix. The weight ratio of solubility agent to biologically active agent is generally between about 1:99 and about 20:1.

Bulking agents typically comprise inert materials. Suitable bulking agents are known to those skilled in the art.

A polymeric sustained release composition of this invention can be formed into many shapes such as a film, a pellet, a cylinder, a disc or a microcarrier. A microcarrier, as defined herein, comprises a polymeric component having a diameter of less than about one millimeter and containing at least one particle of aggregation-stabilized, biologically active agent dispersed therein. A microcarrier can have a spherical, non-spherical or irregular shape. It is preferred that a microcarrier be generally spherical in shape. Typically, the microcarrier will be of a size suitable for injection. A preferred size range for microcarriers is from about 1 to about 180 microns in diameter, such as for injection through a 23-gauge needle.

In the method for preparing aggregation-stabilized agent, the biologically active agent is mixed with a suitable aggregation-stabilizer. It is understood that either or both the agent and stabilizer can be in solid form, typically particulate, or dissolved in an aqueous solution. It is preferred that the agent and stabilizer be combined in single particles, which are more preferably lyophilized.

In the embodiment wherein a biologically active agent is mixed with a metal cation component to form particles, the agent is mixed in a suitable solvent with at least one suitable metal cation component to form a mixture, wherein each component of the mixture can be in suspension or solution, or a combination thereof. The concentration of agent in solution is typically between about 0.1 to about 20 mg agent/ml of solvent, and preferentially, between about 1.0 to about 5.0 mg agent/ml of solvent.

In a preferred embodiment, the agent is contacted with at least one suitable aggregation-stabilizing metal cation, such as $Ca^{+2}$ or $Zn^{+2}$, and with a suitable solvent, under pH conditions suitable for forming a complex of the metal cation and the agent. Typically, the complexed agent will be in the form of a cloudy precipitate, which is suspended in the solvent. However, the complexed agent can also be in solution.

In an embodiment wherein particles of an agent stabilized with a precipitant are formed, the agent is mixed in a suitable aqueous solvent with at least one suitable precipitant to form a stabilizing mixture, wherein each component of the stabilizing mixture can be in suspension or solution, or a combination thereof.

In forming a stabilizing mixture, the content of precipitant is typically between about 10% (w/w) and about 80% (w/w) of the total solids in agent particles and is preferentially more than about 40% (w/w).

It is understood that the agent can be in a solid or a dissolved state, prior to being contacted with the aggregation stabilizer. It is also understood that the aggregation stabilizer can be in a solid or a dissolved state, prior to being contacted with the agent. In a preferred embodiment, a buffered aqueous solution of an agent is mixed with an aqueous solution of the aggregation stabilizer.

Suitable solvents are those in which the agent and the metal cation component are each at least slightly soluble, such as in an aqueous sodium bicarbonate buffer or in an aqueous phosphate buffer or citrate buffer or combinations thereof. For aqueous solvents, it is preferred that water used be either deionized water or water-for-injection (WFI).

The stabilizing mixture is then dried, such as by lyophilization, to form particulate aggregation-stabilized agent. The stabilizing mixture can be bulk lyophilized or can be divided into smaller volumes which are then lyophilized. In a preferred embodiment, the stabilizing mixture is micronized, such as by use of an ultrasonic nozzle, and then lyophilized to form aggregation-stabilized agent particles. Acceptable means to lyophilize the stabilizing mixture include those known in the art. A solid stabilizing mixture can be pressed into pellets.

A suitable pH range can be achieved by dialysis with a buffer, by using the buffer as a solvent for the agent and/or aggregation stabilizer, and by making one or more bulk additions of buffer to the agent solution before, during, and/or after addition of the aggregation stabilizer.

The stabilizing mixture is usually buffered to a pH between about 4.0 and about 8.0 to maintain pH in a range which will prevent a significant loss of biological activity resulting from pH changes during particle formation and/or to support formation of complexes. A preferred pH range is between about 5.0 and about 7.4. Suitable pH conditions are typically achieved through use of an aqueous buffer, such as sodium bicarbonate, as the solvent for the agent and aggregation stabilizer. Typically, the content of buffer in a stabilizing mixture is between about 0.1% (w/w) and about 20% (w/w) of total solids.

Preferably, particles of aggregation-stabilized agent are between about 1 to about 6 micrometers in diameter. The agent particles can be fragmented separately, as described in co-pending U.S. patent application No. 08/006,682, filed Jan. 21, 1993, which describes a process for producing small particles of biologically active agents, which is incorporated herein in its entirety by reference. Alternately, the agent particles can be fragmented after being added to a polymer solution, such as by means of an ultrasonic probe or ultrasonic nozzle.

The formation of $Zn^{+2}$-stabilized IFN or hGH particles are further described in Examples 1 and 4.

In one embodiment for forming a sustained release device, a suitable amount of aggregation-stabilized particles of agent is added to a polymer solution. The agent particles can be dispersed with the polymer solution by stirring, agitation, sonication or by other known mixing means. The polymer solution, having a dispersion of biologically active, aggregation-stabilized agent is then solidified, by appropriate means, to form a sustained release composition of this invention.

Alternately, biologically active, aggregation-stabilized particles of agent and a polymer can be mixed into a polymer solvent sequentially, in reverse order, intermittently, separately or through concurrent additions, to form a dispersion of the agent particles in a polymer solution.

A suitable polymer solution contains between about 1% (w/w) and about 30% (w/w) of a suitable biocompatible polymer, wherein the biocompatible polymer is typically dissolved in a suitable polymer solvent. Preferably, a polymer solution contains about 2% (w/w) to about 20% (w/w) polymer. A polymer solution containing about 5% to about 15% (w/w) polymer is most preferred.

A suitable polymer solvent, as defined herein, is solvent in which the polymer is soluble aggregation-stabilized particles of agent are substantially insoluble and non-reactive. Examples of suitable polymer solvents include polar organic liquids, such as methylene chloride, chloroform, ethyl acetate, acetone methylisobutylketone, n-butylacetate, isobutyl acetate, tetrahydrofuran, methyl acetate and ethyl citrate.

In yet another embodiment of the method of this invention, a metal cation component, not contained in the aggregation-stabilized particles of biologically active agent, is also dispersed within the polymer solution to modulate the release of the biologically active agent.

It is understood that a metal cation component and the aggregation-stabilized particles can be dispersed into a polymer solution sequentially, in reverse order, intermittently, separately or through concurrent additions.

Alternately, a polymer, a metal cation component and the aggregation-stabilized particles can be mixed into a polymer solvent sequentially, in reverse order, intermittently, separately or through concurrent additions.

The method for forming a composition for modulating the release of a biologically active agent from a biodegradable polymer is further described in co-pending U.S. patent application Ser. No. 08/237,057 and co-pending PCT Patent Application PCT/US95/05511.

One suitable method for forming a sustained release composition from a polymer solution is the solvent evaporation method described in U.S. Pat. No. 3,737,337, issued to Schnoring et al., U.S. Pat. No. 3,523,906, issued to Vranchen et al., U.S. Pat. No. 3,691,090, issued to Kitajima et al., or U.S. Pat. No. 4,389,330, issued to Tice et al. Solvent evaporation can be used as a method to form microcarriers and other shaped sustained release devices.

In the solvent evaporation method, a polymer solution containing a dispersion of particles of an aggregation-stabilized biologically active agent, is mixed in or agitated with a continuous phase, in which the polymer solvent is partially miscible, to form an emulsion. The continuous phase is usually an aqueous solvent. Emulsifiers are often included in the continuous phase to stabilize the emulsion. The polymer solvent is then evaporated over a period of several hours or more, thereby solidifying the polymer to form a polymeric matrix having a dispersion of particles of aggregation-stabilized biologically active agent contained therein.

In this method, care must be taken not to heat the polymer solution to a temperature at which denaturing of the biologically active agent in the aggregation-stabilized particles could occur.

Another suitable method for solidifying a polymer solution to form a polymeric matrix, containing particles of aggregation-stabilized biologically active agent, is the phase separation method described in U.S. Pat. No. 4,675,800, which is incorporated herein in its entirety by reference. In this method, polymer within a polymer solution containing aggregation-stabilized particles is precipitated around the particles by the addition of a polymer non-solvent to the polymer solution to form an emulsion, wherein the polymer non-solvent is immiscible with the polymer solvent.

A preferred method for forming aggregation-stabilized microcarriers from a polymer solution uses rapid freezing and solvent extraction as described in U.S. Pat. No. 5,019,400, issued to Gombotz et al. and co-pending U.S. patent application Ser. No. 08/433,726, filed May 18, 1995, the teachings of which are incorporated herein in their entirety by reference. This method of microcarrier formation, as compared to other methods, such as phase separation, additionally reduces the amount of biologically active agent required to produce a sustained release composition with a specific content and also minimizes the loss of biological activity during microparticle formation. Further discussion of the high level of biological activity, typically >98%, maintained in the microparticles of the present invention, formed using this preferred method, is provided in Example 2. Also see Examples 2, 5 and 7 for additional descriptions of microparticle formulations by this method.

In this method, the polymer solution, containing the dispersion of aggregation-stabilized particles, is processed to create droplets, wherein at least a significant portion of the droplets contain polymer solution and aggregation-stabilized particles. These droplets are then frozen by means suitable to form microparticles. Examples of means for processing the polymer solution dispersion to form droplets include directing the dispersion through an ultrasonic nozzle, pressure nozzle, Rayleigh jet, or by other known means for creating droplets from a solution.

Means suitable for freezing droplets to form microparticles include directing the droplets into or near a liquified gas, such as liquid argon and liquid nitrogen to form frozen microdroplets which are then separated from the liquid gas. The frozen microdroplets are then exposed to a liquid non-solvent, such as ethanol, or ethanol mixed with hexane or pentane. The solvent in the frozen microdroplets is extracted as a solid and/or liquid into the non-solvent to form microcarriers containing aggregation-stabilized biologically active agent. Mixing ethanol with other non-solvents, such as hexane or pentane, can increase the rate of solvent extraction, above that achieved by ethanol alone, from certain polymers, such as poly(lactide-co-glycolide) polymers.

A wide range of sizes of sustained release microcarriers can be made by varying the droplet size, for example, by changing the ultrasonic nozzle diameter. If very large microcarriers are desired, the microcarriers can be extruded through a syringe directly into the cold liquid. Increasing the viscosity of the polymer solution can also increase microparticle size. For example, the size of the microcarriers produced by this process can vary over a wide range, such as from greater than about 1000 to about 1 micrometers, or less, in diameter.

Yet another method of forming a sustained release composition, from a polymer solution, includes film casting, such as in a mold, to form a film or a shape. For instance, after putting the polymer solution containing a dispersion of aggregation-stabilized particles into a mold, the polymer solvent is then removed by means known in the art, or the temperature of the polymer solution is reduced, until a film or shape, with a consistent dry weight, is obtained. Film casting of a polymer solution, containing a biologically active agent, is further described in co-pending U.S. patent application Ser. No. 08/237,057.

It is believed that the release of the biologically active agent can occur by two different mechanisms. The agent can be released by diffusion through aqueous filled channels generated in the polymeric matrix, such as by the dissolution of the agent or by voids created by the removal of the polymer's solvent during the synthesis of the sustained release composition. A second mechanism is the release of the agent due to degradation of the polymer.

The rate of polymer degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; the polymer end group; and the molecular weight of the polymer. These properties can affect hydrophilicity and crystallinity, which control the rate of hydration of the polymer. Hydrophilic excipients such as salts, carbohydrates and surfactants can also be incorporated to increase hydration and which can alter the rate of erosion of the polymer.

By altering the properties of the polymer, the contributions of diffusion and/or polymer degradation to the release of biologically active agent can be controlled. For example, increasing the glycolide content of a poly(lactide-co-glycolide) polymer and decreasing the molecular weight of the polymer can enhance the hydrolysis of the polymer and thus, provides an increased agent release from polymer erosion.

In addition, the rate of polymer hydrolysis may be increased in non-neutral pH's. Therefore, an acidic or a basic excipient can be added to the polymer solution, used to form the microcarriers to alter the polymer erosion rate.

The sustained release device of this invention can be administered to a human, or other animal, by injection, implantation (e.g., subcutaneously, intramuscularly, intraperitoneally, intracranially, intravaginally and intradermally), administration to mucosal membranes (e.g., intranasally or by means of a suppository), or in situ delivery (e.g. by enema or aerosol spray) to provide the desired dosage of an agent based on the known parameters for treatment with that agent of the various medical conditions.

The invention will now be further and specifically described by the following examples.

EXAMPLE 1

Formation of Aggregation-Stabilized Interferon

IFN-α,2b, which was used in the present Examples, is identical to IFN-α,2 as described in Rubenstein et al., Biochem. Biophys. Acta, 695: 705–716 (1982), with the exception that the lysine at position 23 of IFN-α,2 is an arginine in IFN-α,2b. The IFN was stabilized by forming a complex with $Zn^{+2}$ ions, wherein the complex has a lower solubility in aqueous solutions than does non-complexed IFN.

The IFN was complexed as follows. The IFN-α,2b was dissolved in different volumes of 10 mM sodium bicarbonate buffer (pH 7.2) to form IFN solutions with concentrations between 0.1 and 0.5 mM IFN. A 10 mM $Zn^{+2}$ solution was prepared from deionized water and zinc acetate dihydrate and then was added to the IFN solutions to form $Zn^{+2}$-IFN solutions with a final IFN concentration of about 1.3 mg/ml and a $Zn^{+2}$:IFN molar ratio of 2:1, 4:1 or 10:1, respectively. The pH of the $Zn^{+2}$-IFN solution was then adjusted to 7.1 by adding 1% acetic acid. A cloudy suspended precipitate, comprising aggregation-stabilized IFN wherein the IFN is stabilized as a complex with $Zn^{+2}$, formed in each solution.

The suspension of aggregation-stabilized IFN was then micronized using an ultrasonic nozzle (Type V1A; Sonics and Materials, Danbury, Conn.) and sprayed into a polypropylene tub (17 cm diameter and 8 cm deep) containing liquid nitrogen to form frozen particles. The polypropylene tub was then placed into a −80° C. freezer until the liquid nitrogen evaporated. The frozen particles, which contained $Zn^{+2}$-stabilized IFN, were then lyophilized to form aggregation-stabilized IFN particles.

EXAMPLE 2

Preparation of PLGA Microcarriers Containing Aggregation-Stabilized IFN

Samples of blocked PLGA (intrinsic viscosity of 0.15 dl/g) obtained from Birmingham Polymers (Birmingham, Ala.) or a hydrophilic unblocked PLGA (intrinsic viscosity of 0.17 dl/g) obtained from Boehringer Ingelheim Chemicals, Inc. (Montvale, N.J.), were dissolved in 10 ml of methylene chloride per gram of PLGA to form polymer solutions. To these polymer solutions were added about 0.033, 0.1 or 0.2 grams of aggregation-stabilized IFN particles per gram of PLGA, formed as described in Example 1 to form polymer solutions with the following formulations:

| Formula | PLGA | Zn:IFN Molar Ratio | IFN:PLGA Mass Ratio | IFN:MgCO$_3$ Mass Ratio | IFN:ZnCO$_3$ Mass Ratio |
|---|---|---|---|---|---|
| 1 | Blocked | 2:1 | 0.2:1 | N/A | N/A |
| 2 | Blocked | 4:1 | 0.2:1 | N/A | N/A |
| 3 | Blocked | 10:1 | 0.2:1 | N/A | N/A |
| 4 | Blocked | 2:1 | 0.1:1 | 1:1 | N/A |
| 5 | Unblocked | 2:1 | 0.033:1 | 1:1 | N/A |
| 6 | Blocked | 2:1 | 0.033:1 | N/A | 3:1 |
| 7 | Blocked | 2:1 | 0.1:1 | N/A | 1:1 |
| 8 | Blocked | 2:1 | 0.1:1 | N/A | 8:1 |

When added to the polymer solution, $MgCO_3$ and $ZnCO_3$ were sieved through a 38 micrometer (#400) sieve. Each formulation was then sonicated using an ultrasonic probe (Virtis, Co., Gardiner, N.Y.) to fragment and suspend aggregation-stabilized IFN particles in the polymer solutions. The size of the sonicated, aggregation-stabilized IFN particles was between about 2–15 microns. The suspension was then placed in a 10 ml gas-tight syringe.

About 400 ml of 100% ethanol per gram PLGA was added to a round polypropylene tub. This solution was frozen by surrounding the tub with liquid nitrogen. The frozen ethanol was then covered with 500 ml of liquid nitrogen per gram of PLGA. The IFN suspension was then pumped from the syringe by a syringe pump (Orion Sage Pump Model 355, Orion Research Inc., Boston, Mass.), at a rate of 1.7 ml/min, into an ultrasonic nozzle (Type V1A, Sonics and Materials, Danbury, Conn.) that was placed above the container containing the frozen ethanol covered with liquid nitrogen. The nozzle atomized the IFN suspension into droplets which froze upon contact with the liquid nitrogen and formed microcarriers which sank to the surface of the frozen ethanol.

The container was placed into a −80° C. freezer, thereby evaporating the liquid nitrogen and allowing the ethanol to melt. As the ethanol thawed, the microcarriers sank into it. The temperature was lowered to −95.1° C. and the methylene chloride was extracted from the microcarriers. After 24 hours, an additional 400 ml of 100% ethanol per gram of PLGA, which was prechilled to −80° C., was added to the container. Three days after the microcarriers were prepared, the ethanol/microcarrier slurry was filtered using a 0.65 micron Durapore™ membrane (Millipore, Bedford, Mass.). The filtered microcarriers were then vacuum dried in a lyophilizer.

EXAMPLE 3

In vitro Release of IFN Encapsulated with Non-Metal Cation Stabilizer Compared to IFN Stabilized with $Zn^{+2}$ Dextran 70 (Spectrum Chemical Manufacturing Co., Gardena, Calif.) was added to a solution of IFN-α,2b in 10 mM sodium phosphate buffer at a weight ratio of 1:1 (Dextran:IFN). The solution was micronized through an ultrasonic nozzle as described in Example 1 and the frozen particles were then lyophilized. The IFN-Dextran particles were subsequently microencapsulated in blocked PLGA as described in Example 2 to form IFN-Dextran microcarriers. Aggregation-stabilized IFN particles (2:1 $Zn^{+2}$:IFN ratio), as described in Example 1, were also microencapsulated as described in Example 2 to form aggregation-stabilized IFN microcarriers.

In vitro dissolution was conducted on the two microcarrier formulations by incubating 20 mg of each type of microcarrier in buffer at 37° C. IFN release from the microcarriers was monitored by BioRad protein assay (BioRad Inc. Richmond, Calif.).

IFN release from the IFN-Dextran microcarriers was linear for the first 10 days with an average release rate of 6.4%/day. The release continued at a rate of 0.4%/day from day 10 to day 14 with a total cumulative release of 66% by day 14. No further release of protein from the microcarriers was detected. The microcarriers were dried down at day 28. The IFN-Dextran remaining was extracted from the microcarriers and the protein was characterized by testing its solubility in water and monomer content by sodium dodecyl sulfate (SDS) polyacrylamide gel electrophoresis (PAGE). Only 18% of the protein remaining inside the microcarriers was water soluble. The insoluble protein was solubilized using SDS and run on a gel. The insoluble material contained 19% covalent aggregates and 81% non-covalent aggregates.

In contrast the microcarriers with the IFN aggregation-stabilized with $Zn^{+2}$ showed linear release for at least 28 days at a rate of 2.7%/day. The analyses indicate the formulation of IFN with zinc is more stable resulting in a longer period of continuous release of protein from the microcarriers.

EXAMPLE 4

Formation of Aggregation-Stabilized hGH

Purified recombinant human growth hormone (hGH), whose DNA sequence is as described in U.S. Pat. No. 4,898,830, issued to Goeddel et al., was used in this Example. The human growth hormone was stabilized by forming a complex with $Zn^{+2}$ ions, wherein the complex has a lower solubility in aqueous solutions than does non-complexed hGH.

The hGH was dissolved in samples of a 4 mM sodium bicarbonate buffer (pH 7.2) to form hGH solutions with concentrations between 0.1 and 0.5 mM hGH. A 0.9 mM $Zn^{+2}$ solution was prepared from deionized water and zinc acetate dihydrate and then was added to the hGH solutions to form $Zn^{+2}$-hGH solution. The pH of the $Zn^{+2}$-hGH solution was then adjusted to between 7.0 and 7.4 by adding 1% acetic acid. A cloudy suspended precipitate, comprising $Zn^{+2}$-stabilized hGH formed. Lyophilized, aggregation-stabilized hGH particles were then formed as described in Example 1.

EXAMPLE 5

Preparation and Analysis of PLGA Microcarriers Containing Biologically Active, Aggregation-Stabilized hGH Microcarriers containing aggregation-stabilized hGH, formed as described in Example 4, were prepared using the method of Example 2 from hydrophilic unblocked PLGA (50:50 PLGA, 9,300 Daltons; RG502H polymer; Boehringer Ingelheim Chemicals, Inc.), blocked PLGA (50:50 PLGA, 10,000 Daltons; Lot #115-56-1, Birmingham Polymers, Inc., Birmingham, Ala.) and unblocked PLGA (50:50 PLGA, 31,000 Daltons; RG503H, Boehringer Ingelheim Chemicals, Inc.) and varying amounts of $ZnCO_3$.

The integrity of the hGH encapsulated in microcarriers was determined by extracting the hGH from the microcarriers. The microcarriers were placed in a tube containing methylene chloride and vortexed at room temperature to dissolve the polymer. Acetone was then added to the tube, which was subsequently vortexed, to extract and collect the hGH. The collected hGH was then freeze-dried and re-constituted in HEPES buffer containing 10 mM EDTA. Appropriate controls were run to ensure that the extraction process did not affect the integrity of the protein.

The integrity of the encapsulated hGH was analyzed by measuring the percent of hGH monomer contained in the hGH sample after encapsulation by size exclusion chromatography (SEC).

The results of SEC analyses of the hGH integrity of hGH sustained release microcarriers were provided below.

| Formulation (polymer; % Zinc Carbonate) | % Monomer (SEC) |
|---|---|
| 31K unblocked; 6% ZnCO3 | 98.6 |
| 31K unblocked; 6% ZnCO3 | 99.2 |
| 31K unblocked; 3% ZnCO3 | 97.7 |
| 31K unblocked; 3% ZnCO3 | 97.8 |
| 31K unblocked; 1% ZnCO3 | 97.6 |
| 31K unblocked; 0% ZnCO3 | 97.8 |
| 31K unblocked; 0% ZnCO3 | 97.1 |
| 10K blocked; 1% ZnCO3 | 98.2 |

-continued

| Formulation (polymer; % Zinc Carbonate) | % Monomer (SEC) |
|---|---|
| 10K blocked; 1% ZnCO3 | 98.4 |
| 8K unblocked; 0% ZnCO3 | 98.5 |
| 10K blocked; 1% ZnCO3 | 98.4 |

The results showed that the encapsulation process did not cause aggregation of the protein.

EXAMPLE 6

Formation of Aggregation-Stabilized EPO

Erythropoietin was derived as described in U.S. Pat. No. 4,703,008. The EPO was dissolved in deionized water to form an aqueous solution having a concentration of approximately 1 mg/ml. Different samples of the EPO solution were then dialyzed against three changes of the appropriate formulation buffer (i.e., 5 mM phosphate buffer (pH 7), 5 mM citrate buffer (pH 7), 5 mM citrate/5 mM phosphate buffer (pH 7) or 10 mM bicarbonate buffer (pH 7)).

Following dialysis, the concentration of EPO in the dialyzed solutions was verified to be approximately 1 mg/ml as determined by measuring absorbance at 280 nm ($\epsilon$=1.345 L gm$^{-1}$ cm$^{-1}$).

Portions of the dialyzed EPO solutions were then mixed with concentrated solutions of candidate anti-aggregation agents (i.e., ammonium sulfate, zinc acetate, mannitol/sucrose or mannitol/maltose) to form the EPO formulations provided in Table I below. The candidate anti-aggregation agent solutions also possibly contained additional excipients (i.e, inulin, glycine and TWEEN 20™ surfactant).

The anti-aggregation agent solutions were separately prepared in the same buffers used to dialyze the EPO solutions to which they were subsequently added.

Approximate volumes of each anti-aggregation agent solution and of additional buffer were added to a 50 ml polypropylene tube to achieve the desired concentrations for the formulations (described in Table I). Each dialyzed EPO solution was then added to the appropriate anti-aggregation agent solution and then the solutions were mixed by gentle inversion.

TABLE I

| | Formulations (wt %) | | | | | | | |
|---|---|---|---|---|---|---|---|---|
| | Am1 | Am4 | Am7 | Ma1 | Ma3 | Ma4 | Zn1 | Zn6 |
| EPO | 10.0 | 10.1 | 9.9 | 10.0 | 10.0 | 10.0 | 10.0 | 10.0 |
| Ammonium Sulfate | 66.8 | 64.7 | 79.1 | 0.0 | 0.0 | 0.0 | 0.0 | 0.0 |
| Zinc Acetate | 0.0 | 0.0 | 0.0 | 0.0 | 0.0 | 0.0 | 76.9 | 76.9 |
| Mannitol | 0.0 | 0.0 | 0.0 | 62.5 | 62.5 | 72.5 | 0.0 | 0.0 |
| Sucrose | 0.0 | 0.0 | 0.0 | 10.0 | 0.0 | 10.0 | 0.0 | 0.0 |
| Maltose | 0.0 | 0.0 | 0.0 | 0.0 | 10.0 | 0.0 | 0.0 | 0.0 |
| 5 mM Citrate Buffer (pH 7) | 0.0 | 15.1 | 0.0 | 0.0 | 0.0 | 0.0 | 0.0 | 0.0 |
| 5 mM Phosphate Buffer (pH 7) | 0.0 | 0.0 | 10.0 | 7.5 | 7.5 | 7.5 | 0.0 | 0.0 |
| 5 mM Citrate/ 5 mM Phosphate Buffer (pH 7) | 22.1 | 0.0 | 0.0 | 0.0 | 0.0 | 0.0 | 0.0 | 0.0 |
| 10 mM Bicarbonate Buffer (pH 7) | 0.0 | 0.0 | 0.0 | 0.0 | 0.0 | 0.0 | 13.1 | 12.1 |
| Inulin | 1.1 | 10.1 | 1.0 | 0.0 | 0.0 | 0.0 | 0.0 | 0.0 |
| Glycine | 0.0 | 0.0 | 0.0 | 10.0 | 10.0 | 0.0 | 0.0 | 0.0 |
| TWEEN 20 ™ Surfactant | 0.0 | 0.0 | 0.0 | 0.0 | 0.0 | 0.0 | 0.0 | 1.0 |

Lyophilized, aggregation-stabilized EPO particles were then formed from the EPO solutions as described in Example 1. The EPO particles were removed from the lyophilizer under an atmosphere of dry nitrogen, handled in a low humidity environment, and stored desiccated at −80° C.

EXAMPLE 7

Preparation and Analysis of PLGA Microcarriers Containing Aggregation-Stabilized Erythropoietin Microcarriers containing the aggregation-stabilized EPO formulations of Example 6 were prepared from unblocked (50:50; MW 10,000 Daltons) PLGA, obtained from Boehringer Ingelheim Chemicals, Inc., Montvale, N.J., or blocked (50:50; MW 10,000 Daltons) PLGA obtained from Birmingham Polymers, Inc., Birmingham, Ala.

In addition, microcarriers, containing the Am7 formulation of aggregation-stabilized EPO particles, were prepared from unblocked (50:50) PLGA with a molecular weight of approximately 31,000 Daltons or 45,000 Daltons, (Boehringer Ingelheim Chemicals, Inc., Montvale, N.J.).

The method described in Gombotz et al. (U.S. Pat. No. 5,019,400), and in Example 2, was used to encapsulate the aggregation-stabilized EPO particles of Example 6 in PLGA. In each case, polymer was dissolved in 5.1 ml of methylene chloride to form a polymer solution. Magnesium carbonate, or zinc carbonate, was sieved through a 38 micrometer sieve and was then added to the polymer solution to a final concentration of 10% w/vol. The polymer/salt suspension was subsequently combined with 30 mg of aggregation-stabilized EPO particles.

The polymer solution, containing suspended salt and EPO particles, was placed in an ice-water bath and sonicated using an ultrasonic probe (Virtis Co., Gardiner, N.Y.) to reduce the protein particle size to approximately 2 to 3 micrometers in diameter and to form a dispersion of EPO particles within the polymer solution.

Microcarriers containing aggregation-stabilized EPO were prepared using the method described in Example 2.

The immunoreactivity of the EPO in these sustained release microcarriers was subsequently determined by extracting protein and analyzing by radioimmunoassay (RIA) (Incstar: Stillwater, Minn.). To extract the EPO from the microcarriers, approximately 10 mg of microcarriers were placed in a tube with 250 µl of methylene chloride. The samples were vortexed for 10 to 20 seconds and left at room temperature for 5 minutes to dissolve the polymer. A sample of acetone (750 µl) was added, vortexed for an additional 10 seconds, and centrifuged at 14,000 rpm for 30 seconds at 4° C. to pellet the EPO. The supernatant was removed and the methylene chloride and acetone steps were repeated twice more. Samples were dried in a lyophilizer or vacuum oven for 14–18 hours at room temperature. The EPO pellet was reconstituted in 1 ml HEPES buffer by vortexing for about 10 seconds, then standing at room temperature for about 1 hour until completely dissolved. The extracted EPO was diluted in buffer (8.1 mM $Na_2HPO_4$, 1.5 mM $KH_2PO_4$, 400 mM NaCl, pH 7.5) to a concentration of approximately 25 µg/ml for analysis.

The immunoreactivity of the EPO was found to be 121,000±5000 units per mg of EPO. This specific activity is comparable to the range obtained for bulk EPO (130,000–140,000 units per mg of EPO) thus showing an insignificant reduction of EPO activity due to the method of forming the sustained release compositions of the present invention. Monomer content was found to be greater than 98% for all microcarriers.

The microcarriers containing Am1 and Am7 EPO particles were also assayed for EPO dimer, by size exclusion chromatography (SEC), and for high molecular weight EPO aggregates by SDS-PAGE/Western blot analysis. No EPO dimer or high molecular weight aggregates were detected.

EXAMPLE 8

In Vitro Release of EPO from Aggregation-Stabilized EPO Microcarriers

The in vitro release kinetics of EPO from aggregation-stabilized particles within PLGA microcarriers were assessed in HEPES buffer (75 mM HEPES, 115 mM NaCl, 0.1% (by volume) TWEEN 20™, 0.1% (by weight) sodium azide titrated to pH 7.4 with NaOH) or in HEPES buffer containing 2% or 20% sheep serum. The studies were conducted by suspending 8–10 mg of microcarriers in 1–5 ml of buffer at 37° C. At specified time points, the buffer was removed in full and replaced with fresh buffer.

Figure 2:
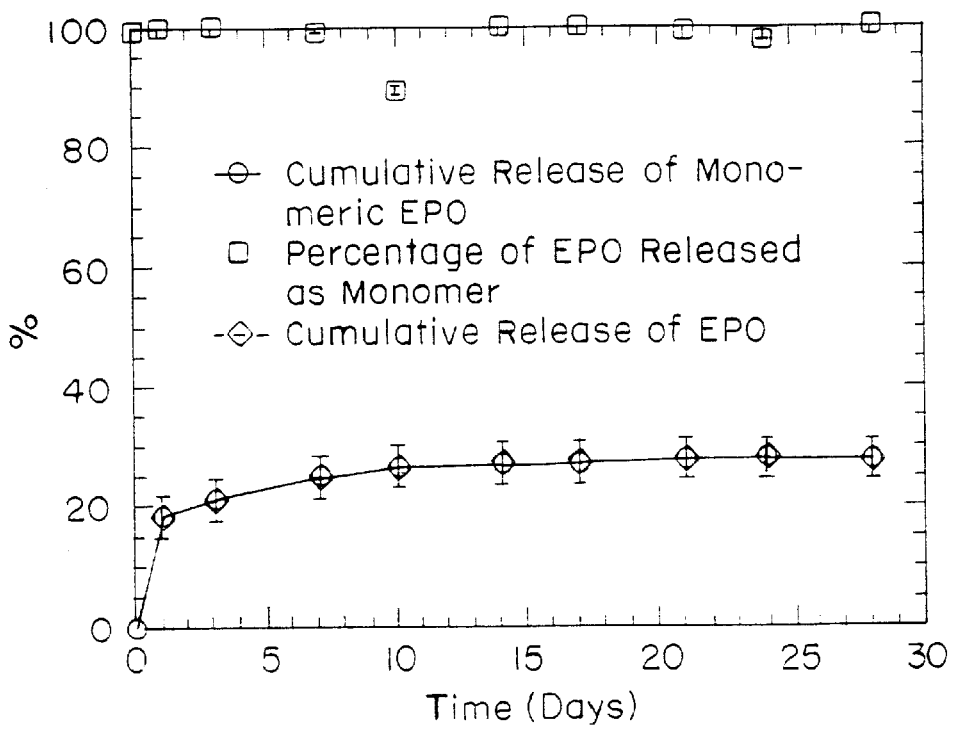

In samples incubated in HEPES buffer, the releases over time of EPO monomer (biologically active EPO) and of EPO aggregates (biologically inactive EPO) were determined by size exclusion chromatography (SEC). The results of the SEC analyses upon in vitro release kinetics in HEPES buffer of various microcarriers, wherein the microcarriers were a) unblocked PLGA (MW 10,000 Daltons) microcarriers containing formulations Am1 or Am7, and b) blocked PLGA (MW 10,000 Daltons) microcarriers containing Zn1, are provided in FIGS. 1, 2 and 3, respectively. FIGS. 1 and 2 show the EPO released from formulations containing ammonium sulfate as an anti-aggregation agent was almost all monomeric EPO over the length of the release period.

Figure 3:
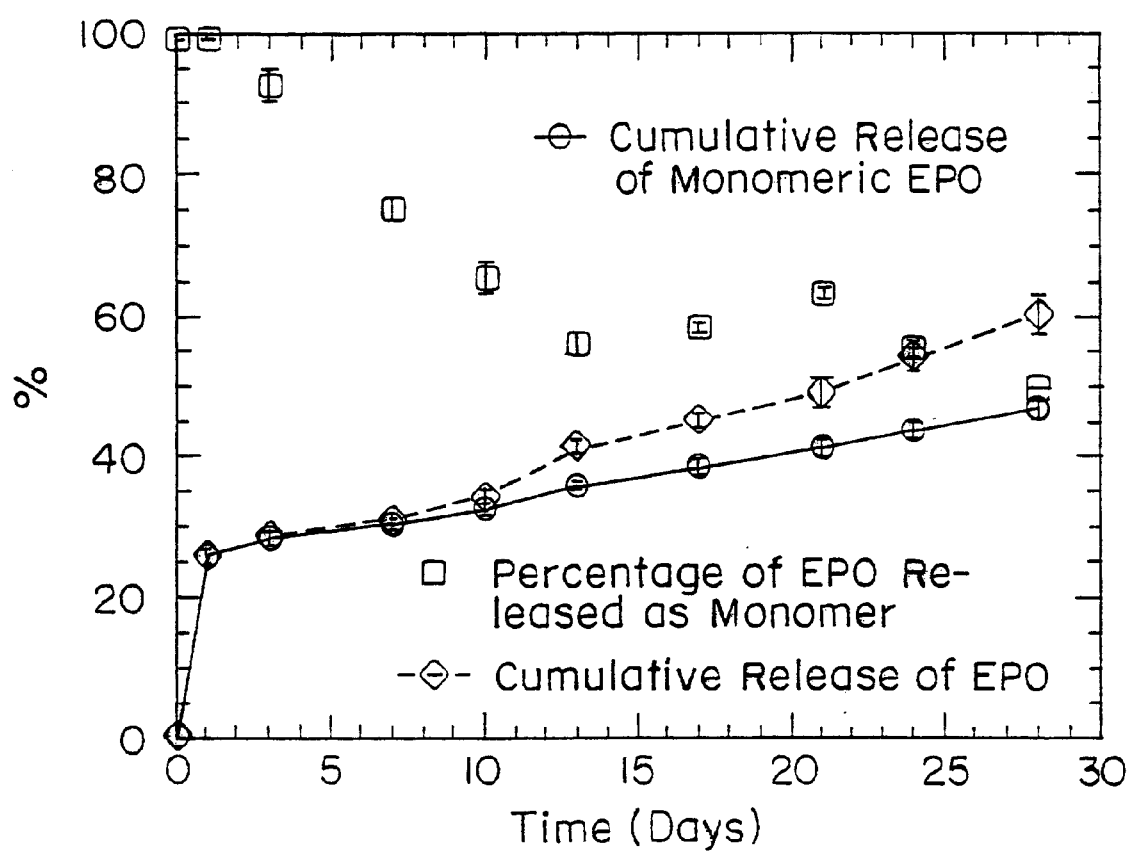
Figure 4:
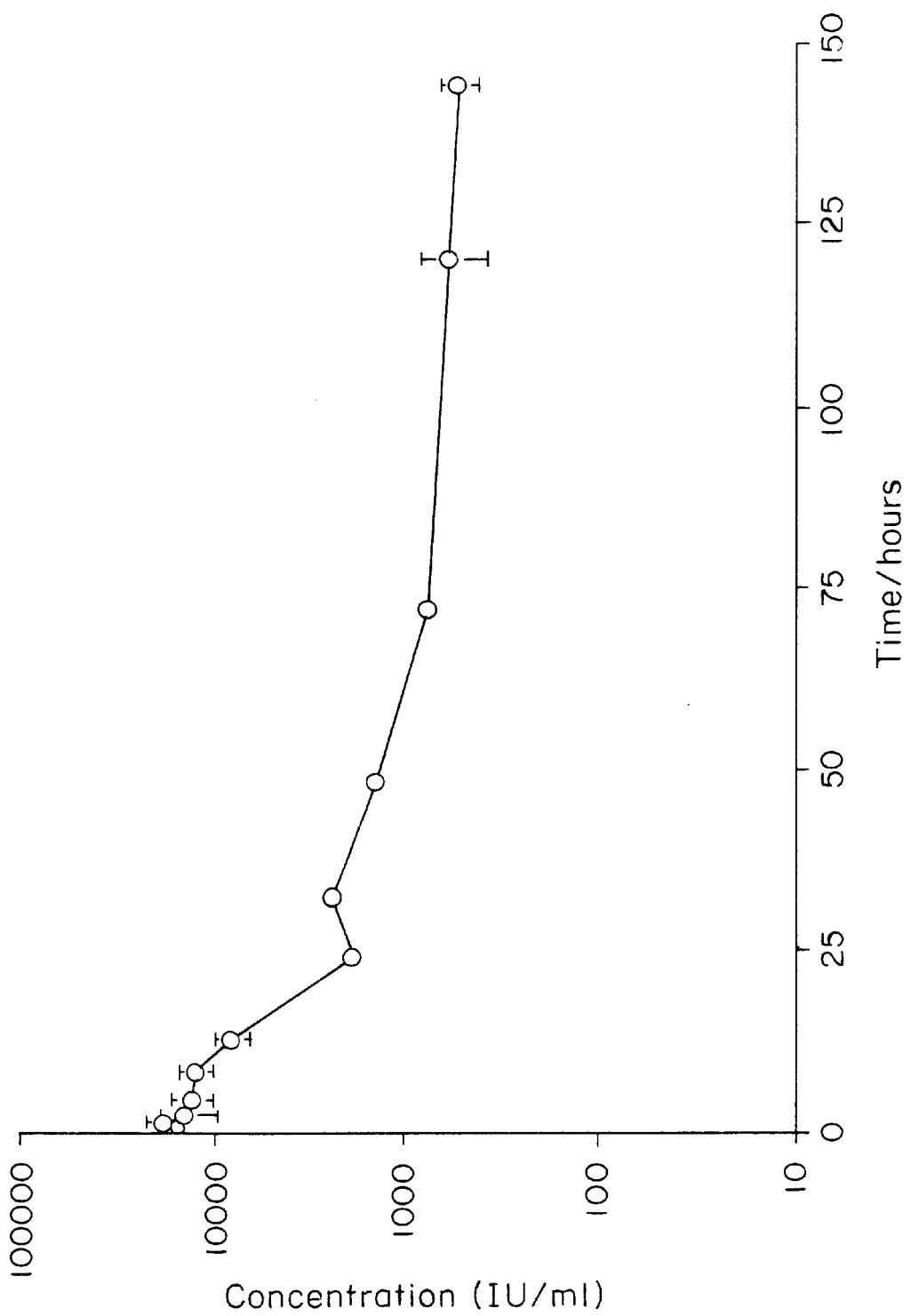
Figure 5:
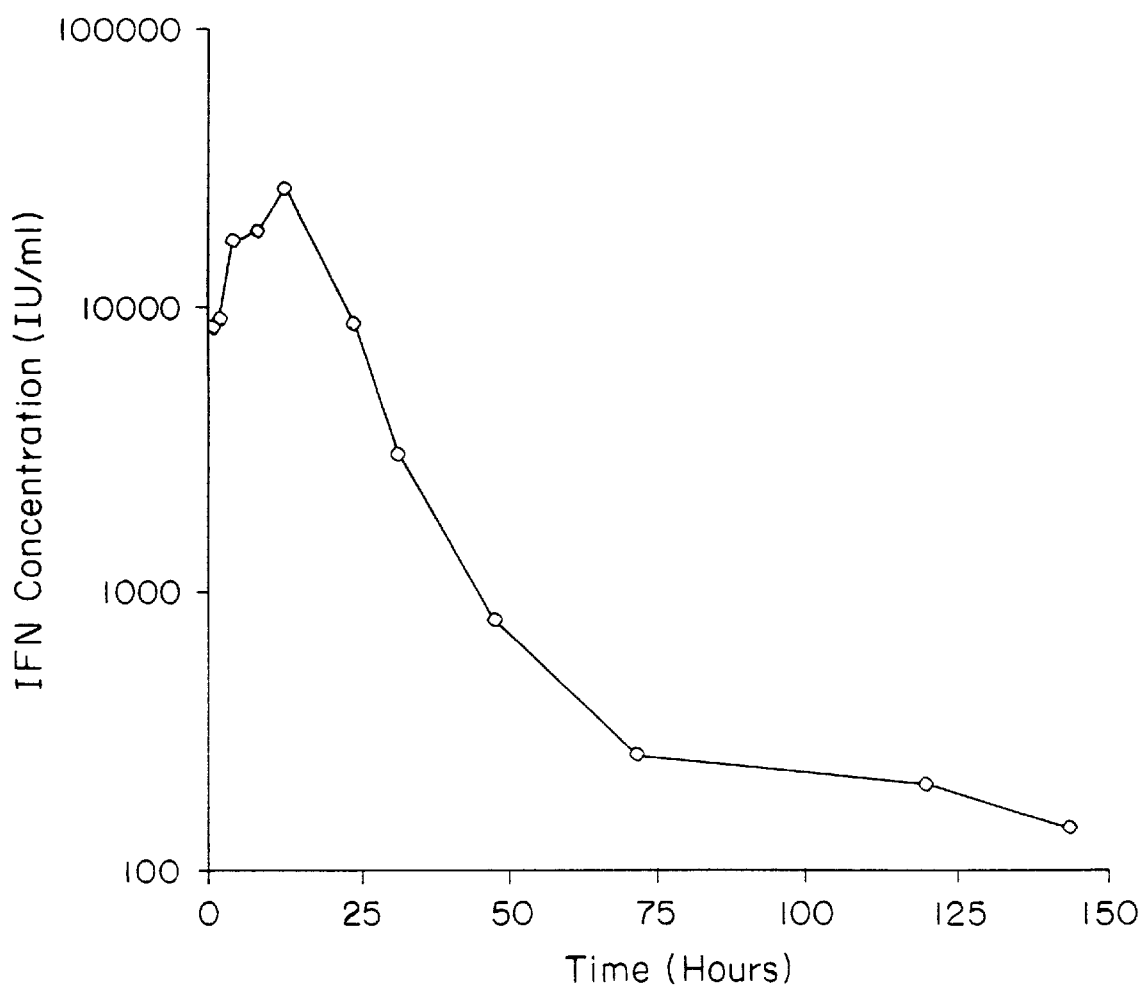
Figure 6:
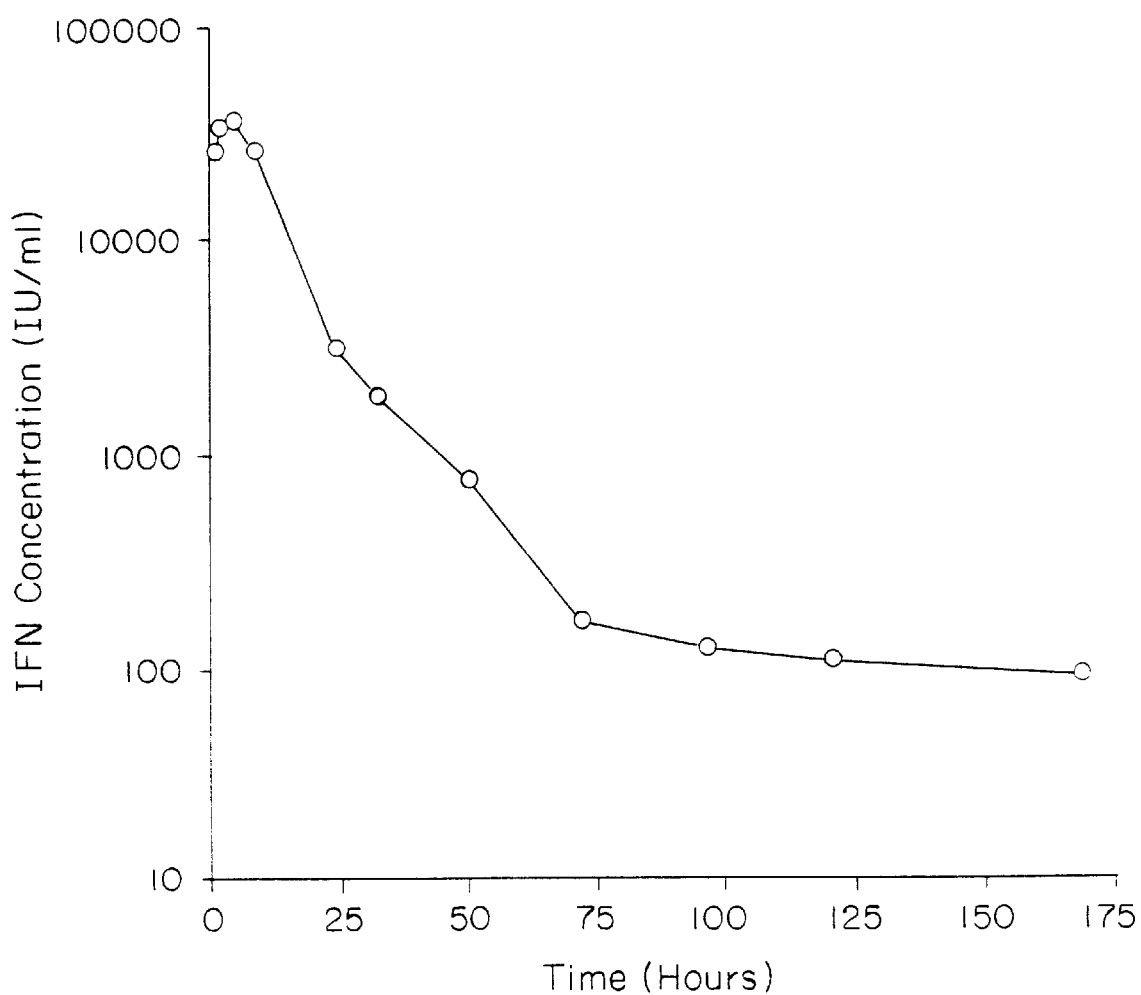
Figure 7:
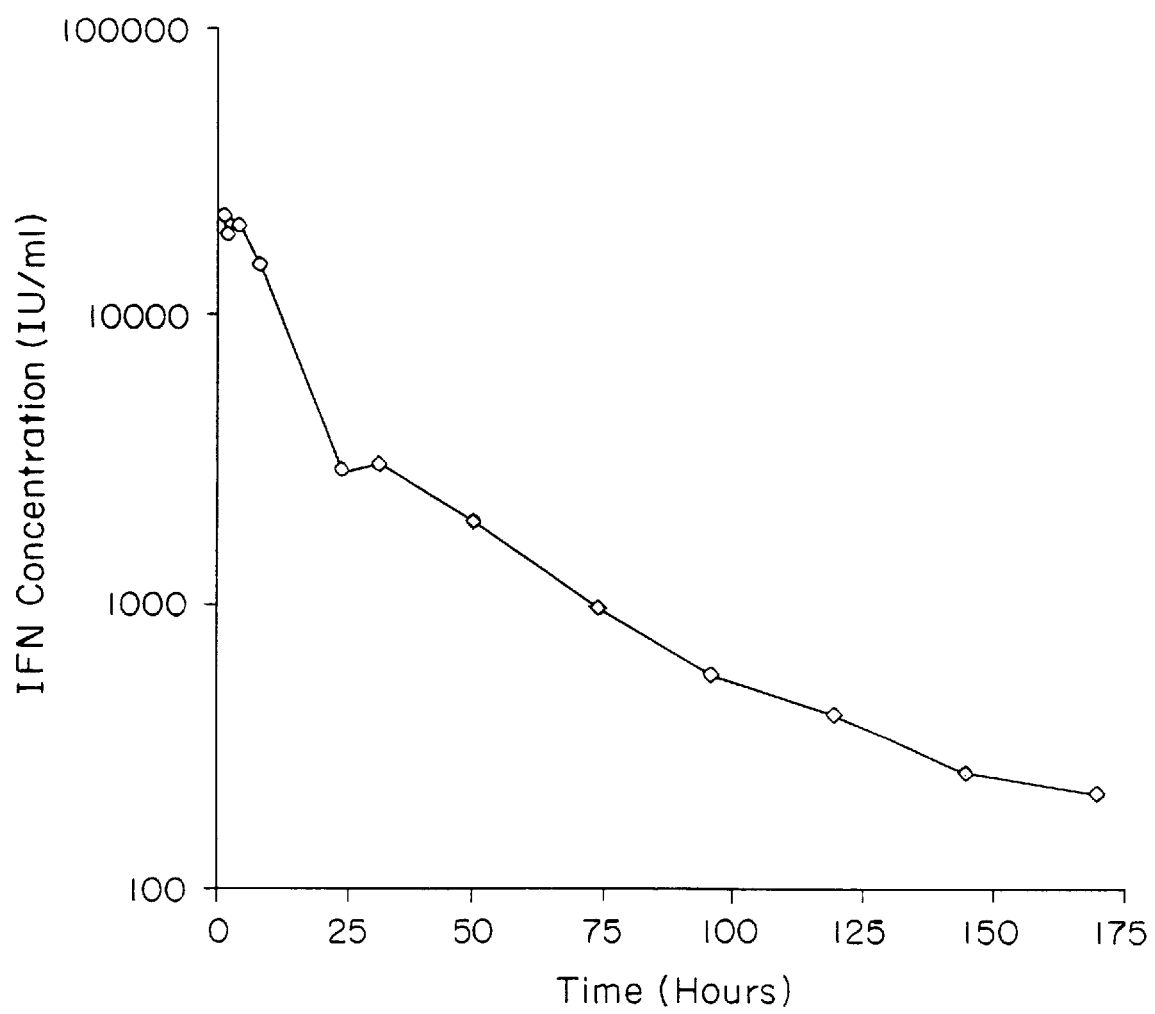
Figure 8:
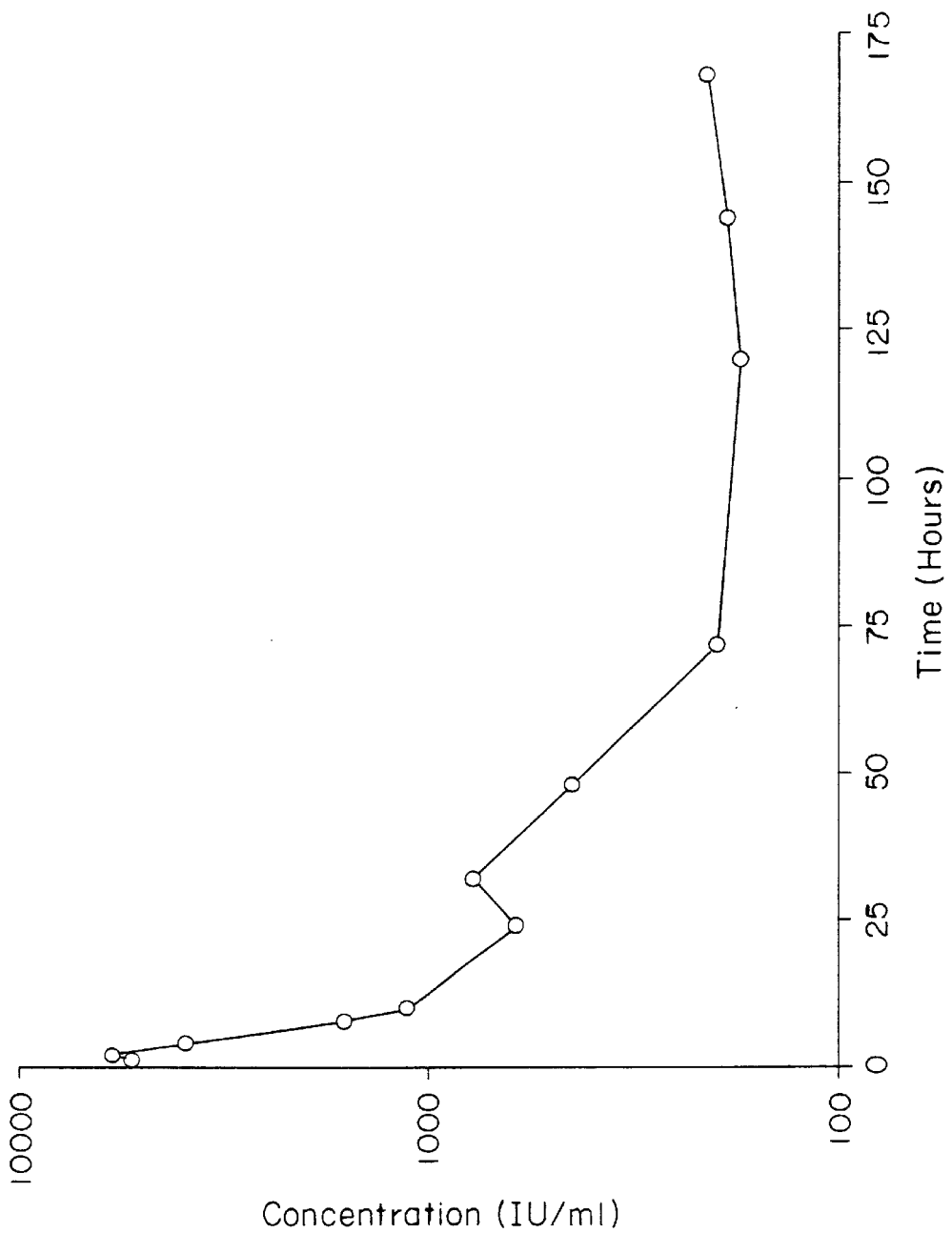
Figure 9:
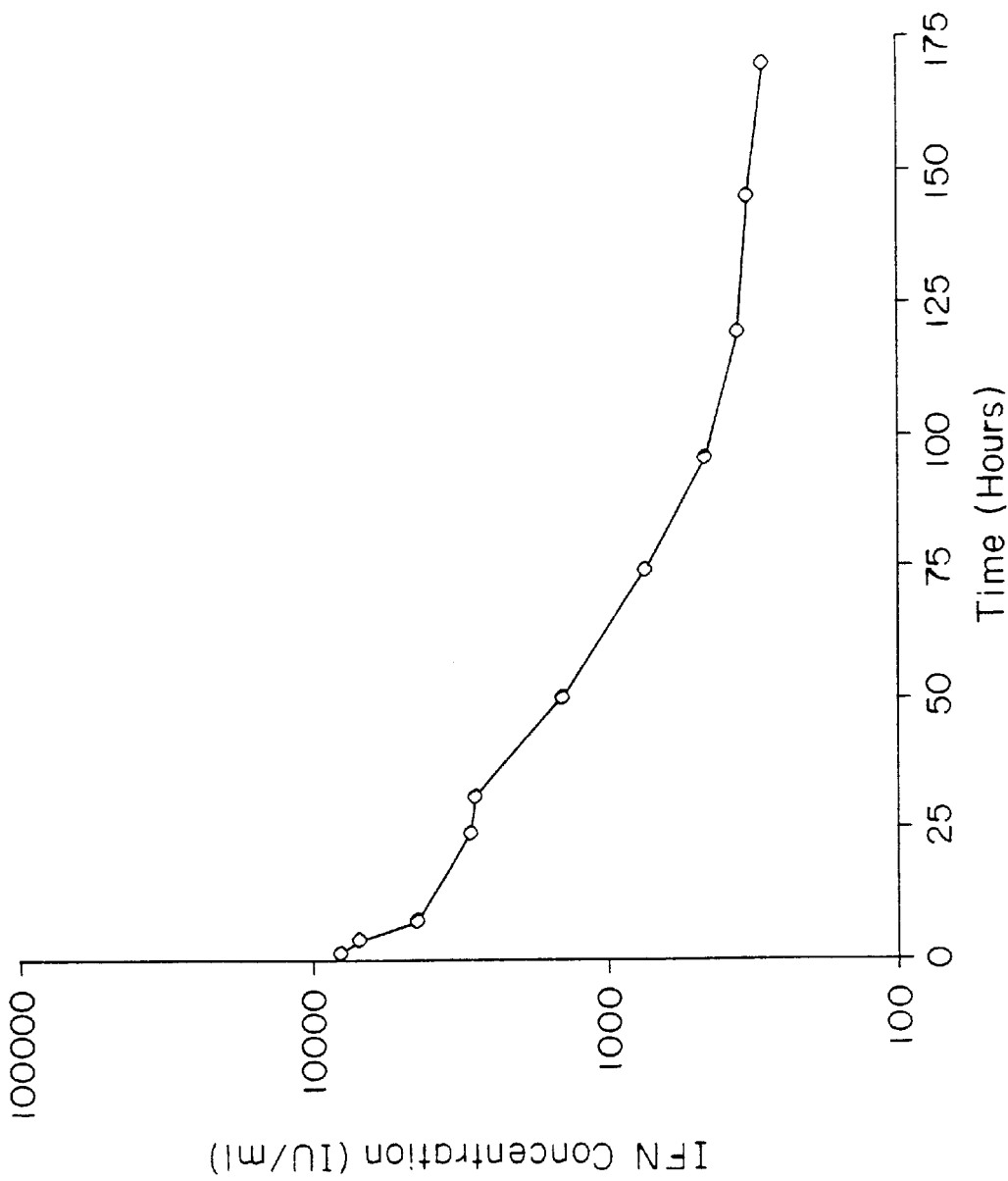
Figure 10:
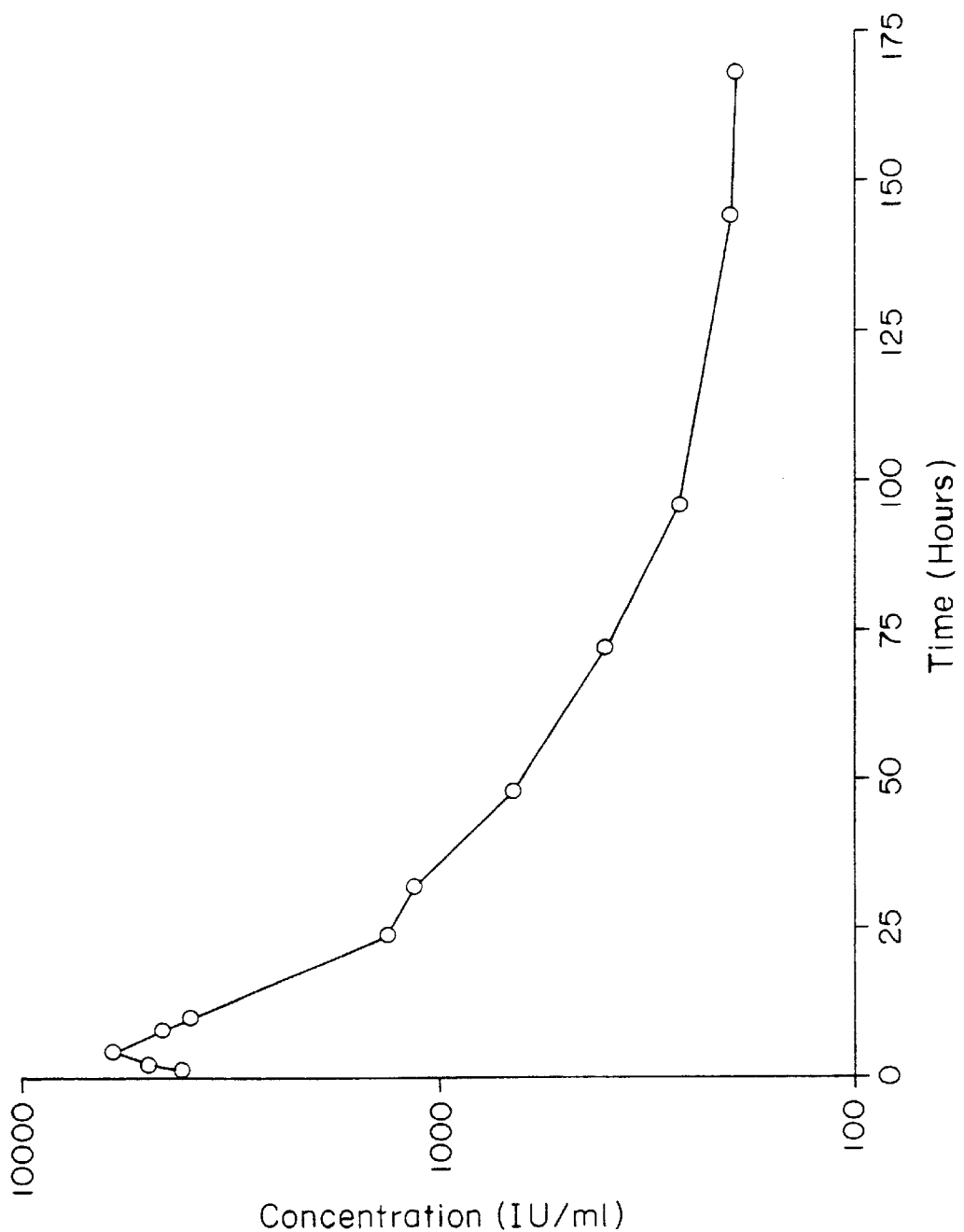

FIG. 3 shows the EPO released from a formulation containing zinc acetate, as an anti-aggregation agent, contained significant levels of aggregate which increased substantially over the length of the release period.

The results of the SEC and RIA analyses upon in vitro release kinetics in HEPES buffer, and in HEPES/serum, of various microcarriers (all in 10,000 Dalton PLGA) which contained different EPO formulations of Example 6 are provided in Table II. The initial burst and release rate were determined in the HEPES/serum test by RIA. The integrity of the released EPO was assessed in HEPES buffer by SEC.

TABLE II

| Formula | EPC Load (%) | Polymer/ Salt | Aggregate Released (% init. load) | Initial Burst (%) | Average Release (%/day) | Release Duration (days) |
|---|---|---|---|---|---|---|
| Zn1 | 10 | Blocked/ 10% $MgCO_3$ | 12 | 66 | 1.2 | 14 |
| Zn1 | 10 | Blocked/ 10% $ZnCO_3$ | 22 | 46 | 1.7 | 28 |
| Zn6 | 10 | Blocked/ 10% $ZnCO_3$ | 37 | 32 | 1.6 | 28 |
| Am1 | 5 | Unblocked/ 10% $MgCO_3$ | 1 | 39 | 1.4 | 21 |
| Am1 | 10 | Blocked/ 10% $MgCO_3$ | 2 | 71 | 0.3 | 3 |
| Am4 | 5 | Unblocked/ 10% $MgCO_3$ | 1 | 29 | 1.1 | 21 |
| Am4 | 5 | Unblocked/ none | 1 | 35 | 0.9 | 28 |
| Ma1 | 5 | Unblocked/ 10% $MgCO_3$ | 1 | 44 | 1.8 | 24 |
| Ma3 | 10 | Unblocked/ 10% $MgCO_3$ | 1 | 71 | 1.3 | 21 |
| Ma4 | 10 | Blocked/ 10% $ZnCO_3$ | 1 | 77 | 0.6 | 3 |

These analyses show that the addition of suitable anti-aggregation agents significantly reduced the aggregation of EPO over the release periods. These analyses also demonstrated that the addition of a metal cation component (e.g., salt) to the polymer, as well as the selection of the type of polymer (i.e., blocked or unblocked) significantly affected the initial burst level and the duration of release.

EXAMPLE 9

Integrity of EPO Released In Vitro from Aggregation-Stabilized EPO Microcarriers The purpose of the experiment was to determine the integrity of EPO released from PLGA microcarriers having varying concentrations of ammonium sulfate.

Aggregation-stabilized EPO formulations comparable to Am7, except having 10%, 20%, or 40% ammonium sulfate, were prepared as described in Example 6. The eliminated ammonium sulfate was replaced with sodium chloride or sucrose such that the total weight of ammonium sulfate and sodium chloride or sucrose was 79%.

The percent monomeric and aggregate EPO were determined after 35 days and 42 days release in vitro. The Am7 formulation, as well as the 40% ammonium sulfate/NaCl formulation produced 3–4% aggregates at both time points, whereas the 10% and 20% ammonium sulfate/NaCl formulations produced 5–6% aggregates. Mannitol formulations produced results similar to the 10% and 20% ammonium sulfate formulations.

In the case where ammonium sulfate was replaced with sucrose, there was not sufficient drug released from the 40% ammonium sulfate formulation to quantitate. The 10% and 20% ammonium sulfate formulations with sucrose, like their sodium chloride counterparts, showed more aggregates (6–9%) than were observed with the Am7 formulation.

EXAMPLE 10

In Vivo Release of Aggregation-Stabilized IFN-α, 2b From Polymeric Microcarriers in Rats Microcarriers, containing aggregation-stabilized IFN, which were prepared as described in Example 2, were tested in rats for the in vivo release of IFN-α,2b. Normal rats were obtained from Taconics, Inc. (Germantown, N.Y.). The animals were fed with a standard diet and allowed free access to water. Three to four rats were injected subcutaneously in the interscapular region with a dose of 0.6–2.0 mg of IFN/kg, in a 0.5% gelatin, 1% glycerol and 0.9% w/w NaCl vehicle, on day 0 for each of the IFN microcarriers of Example 2. Blood samples were taken from the tail vein of each rat at 1, 2, 4, 8, 10 (optionally), 24, 36 and 48 hours after injection. Additional blood samples were then taken approximately once a day for the following 4–5 days. The IFN concentration in the rat serum samples was determined using an IFN-α immunoradiometric assay, (Celltech, Slough, U.K), hereinafter "IRMA". The IRMA assay has a minimum limit of detecting of 6 IU/ml. The IFN serum levels for control rats, which did not receive the microcarriers containing $Zn^{+2}$-stabilized IFN were found to be less than 6 IU/ml.

The results of the IRMA assays conducted on the rats receiving the microcarriers of Example 2 are shown in FIGS. 4–10. FIGS. 4–10 show that these injectable microcarrier formulations provided a sustained release of immunologically active IFN-α.

EXAMPLE 11

In Vivo Release of Aggregation-Stabilized IFN From Polymeric Microcarriers in Immunosuppressed Rats One group of male Sprague-Dawley rats (N=2) (control group), weighing 400±50 g (S.D.) was injected as described in Example 10 with the microcarriers of Formula 8 of Example 2. An additional group (N=2) of rats (test group) was also given daily intraperitoneal injections of 10 mg cyclosporin A (Sandimmune® Injection, Sandoz, East Hanover, N.J.) and 5 mg hydrocortisone (Spectrum Co., Gardena, Calif.) in 0.5 ml sterilized saline for injection (USP) per Kg of body weight for days 0 to 14 and then injections twice a week for days 15 to 28. These injections were to suppress the response of the rats' immune systems to the release of IFN-α,2b in vivo. No antibody titers were detected in these rats for the duration of treatment.

This method of immunosuppression is further described in co-pending U.S. patent application Ser. No. 08/480,813, filed Jun. 7, 1995.

The control group did not receive injections to suppress their immune response to IFN-α,2b. Antibodies were detected after day 7 in these rats.

Figure 11:
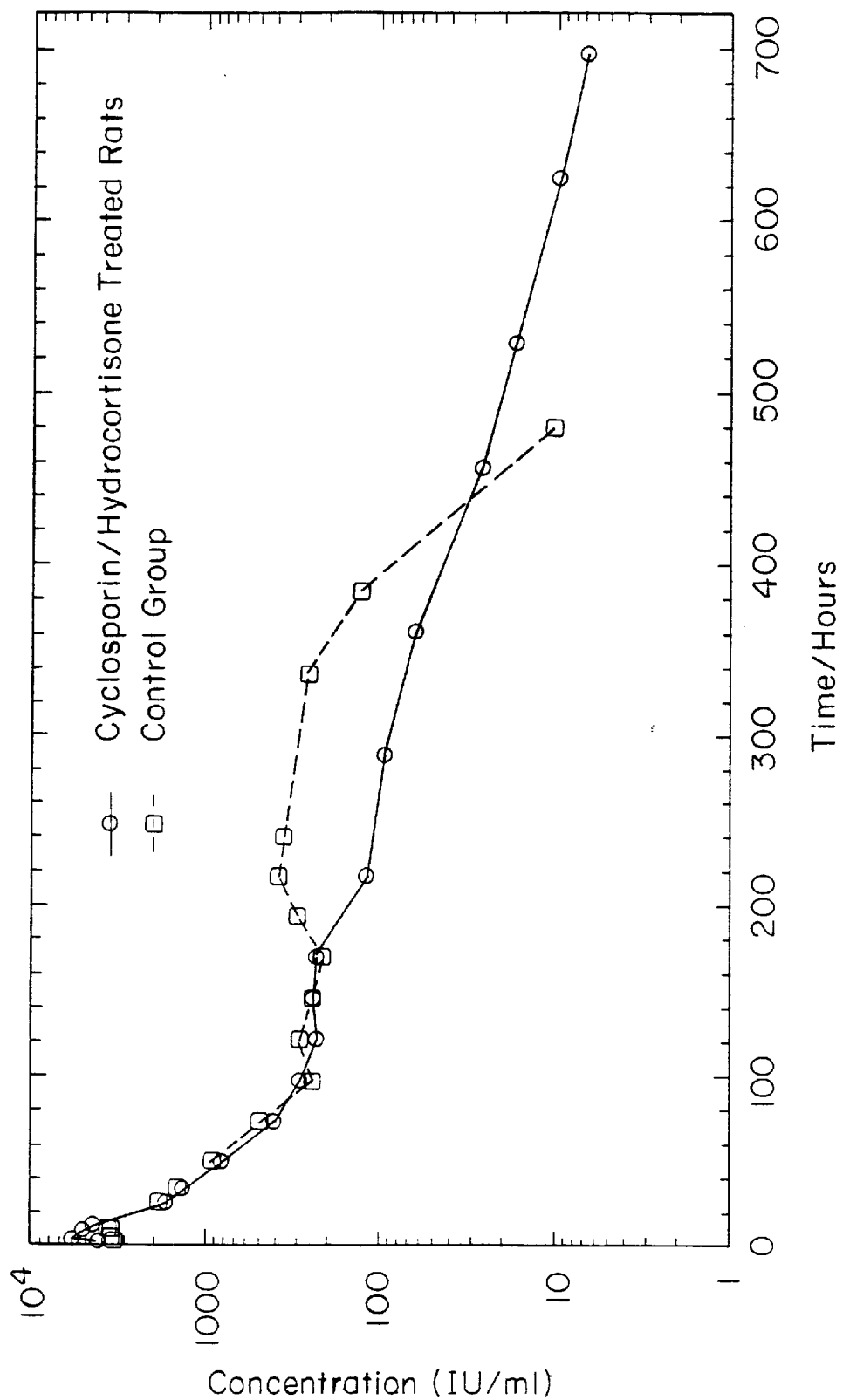

The serum levels of IFN-α,2b in the rats of the experimental group and the control group were determined by IRMA through day 29 (696 hours and 480 hours, respectively). These results are provided in FIG. 11. The results for both groups are the same through day 7 suggesting that the cyclosporin A/hydrocortisone treatment does not affect the measured serum concentrations of IFN. The results show that the control group serum levels measured for IFN were artificially high due to their production of antibodies to the IFN-α,2b. The results for the experimental group, in which antibody formation was suppressed, showed sustained release of IFN-α,2b for up to at least 29 days for the preferred microcarriers (Formula 8) of Example 2.

EXAMPLE 12

In Vivo Release of IFN-α,2b from Aggregation-Stabilized IFN Microcarrier in Monkeys Microcarriers (Formula 8), as prepared as in Example 2, were tested in a test group of four male cynomolgous monkeys (Charles River Primates) for release of IFN-α,2b. The animals were fed with a standard diet and allowed free access to water. Each monkey was injected subcutaneously with a dose of about 0.12 mg IFN/kg monkey on day zero.

Concurrently, each monkey in a control group of four monkeys, with the same diet and water access as the test group, were subcutaneously injected with an aqueous saline solution containing about 0.12 mg IFN/kg monkey.

Blood samples were taken from the femoral vein at 0, 1, 3, 6, 12, 24, 48, 96, 120, 144, 168, 240, and 336 hours after injection. The IFN-α,2b concentration in the monkey serum samples was determined using both a cytopathic effect assay (CPE; *Pharmacopeial Previews, United States Convention, Inc.*, November–December 1990, page 1241) and IRMA. The CPE results for both groups are provided in FIG. 12.

For the test group, the IRMA and CPE results were similar and showed sustained release of IFN-α,2b from the microcarriers.

The CPE and IRMA results for the control group, which received the aqueous IFN-α,2b injection, showed that the IFN-α,2b concentration fell below detectable limits before the second day of testing.

Figure 12:
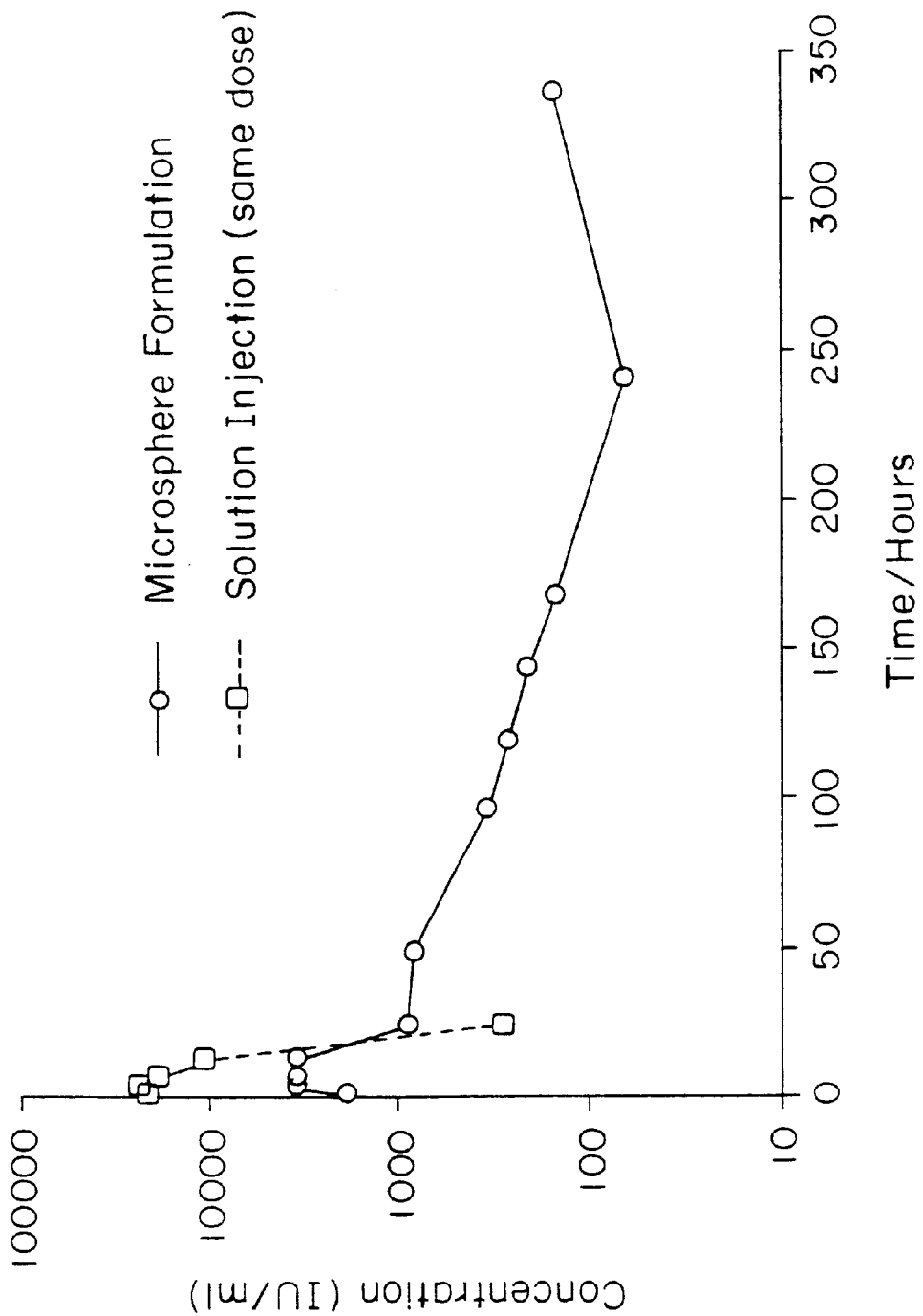
FIG. 12 is a plot of the serum concentrations (IU/ml) of IFN-α,2b versus time over a 14 day interval in monkeys which were subcutaneously administered a) IFN-α,2b controlled release microcarriers of Example 2 having a 1:8 zinc carbonate to IFN-α,2b ratio and b) an equal dose of IFN-α,2b in 0.9% saline solution.

FIG. 12 shows that the microcarrier formulation injected provided sustained release of biologically active IFN-α.

EXAMPLE 13

Assay for hGH After in Vivo Degradation of Aggregation-Stabilized hGH Microcarriers Microcarriers of blocked-PLGA, containing 15% w/w $Zn^{+2}$-stabilized hGH and 0%, 6%, 10% or 20% $ZnCO_3$ were formed by the method of Example 5. Groups of test rats were injected subcutaneously with 50 mg samples of the different hGH microcarriers. The rats were sacrificed after 60 days and the skin samples were excised from the injection sites.

The excised skin samples were placed in 10% Neutral Buffered Formalin for at least 24 hours. They were then trimmed with a razor blade to remove excess skin and placed in PBS.

Tissue samples were processed by Pathology Associates, Inc. (Frederick, Md.). The skin samples were embedded in glycomethacrylate, sectioned and assayed for the presence of hGH using a HistoScan/LymphoScan Staining Kit (Product #24-408M; Accurate Chemical & Scientific Corp., Westbury, N.Y.) according to the manufacturer's instructions. Tissue samples were scored for the presence or absence of staining which was indicative of the presence or absence of hGH in the sample.

All skin samples, associated with hGH microcarrier injections, tested positive for the presence of hGH thus indicating that the blocked-PLGA microcarriers still contained hGH after 60 days in vivo.

The method described in Example 5 was used to form microcarriers by encapsulating 0% or 15% w/w hGH, in the form of Zn:hGH complex, and also 0%, 1% or 6% w/w $ZnCO_3$ salt, within blocked-PLGA and within unblocked-PLGA.

In vivo degradation of unblocked-PLGA microcarriers versus blocked-PLGA microcarriers were compared by injecting samples of microcarriers into rats and then analyzing the microcarriers remaining at the injection site at various times post-injection. Three rats were assayed at each time point for each microcarrier sample. On the day of administration of the microcarriers, 750 μl of vehicle (3% carboxymethyl cellulose (low viscosity) and 1% Tween-20 in saline) was added to vials containing 50±1 mg of microcarriers. Immediately, the vials were shaken vigorously to form a suspension which was then aspirated into a 1.0 cc syringe without a needle.

Rats (Sprague-Dawley males) were anesthetized with a halothane and oxygen mixture. The injection sites (intrascapular region) were shaven and marked with a permanent tatoo to provide for the precise excision of skin at the sampling time points. Each rat was injected with an entire vial of microcarriers using 18 to 21 gauge needles.

On designated days (days 15, 30, 59 and 90 post-injection for animals receiving blocked-PLGA microcarriers, or days 7, 14, 21, 28 and 45 p post-injection on for animals receiving unblocked-PLGA microcarriers) the rats were sacrificed by asphyxiation with $CO_2$ gas and the skin at the injection sites (including microcarriers) was excised. Since the microcarriers tended to clump at the injection sites, the presence or absence of microcarriers was determined visually.

The visual inspections found that the unblocked-PLGA microcarriers degraded substantially faster than the blocked-PLGA microcarriers, and that the addition of $ZnCO_3$ to the blocked-PLGA substantially slowed polymeric degradation. For example, in the rats injected with unblocked-PLGA microcarriers containing 0% hGH and 0% or 1% $ZnCO_3$, no microcarriers were visible on day 21. In addition, for rats injected with blocked-PLGA microcarriers containing 0% hGH and 0% $ZnCO_3$, a few microcarriers were visible on day 60 and none were visible on day 90. Furthermore, for rats injected with blocked-PLGA microcarriers containing 0% or 15% hGH and 6% $ZnCO_3$, microcarriers were visible on day 90.

EXAMPLE 14

In Vivo Release of Aggregation-Stabilized hGH Microcarriers in Rats

Studies were conducted in rats to screen various hGH microcarrier formulations, determine pharmacokinetic parameters following intravenous (IV), subcutaneous (SC) and SC osmotic pump (Alzet®) administration of hGH, and to evaluate serum profiles and in vivo release rate of various hGH microcarrier formulations.

Sprague-Dawley rats were divided into groups of three each, randomized by body weight, and one hGH microcarrier formulation was administered to each group. Rats were injected subcutaneously with approximately 7.5 mg of hGH in 50 mg of microcarriers, suspended in 0.75 ml of an aqueous injection vehicle. The vehicle composition was 3% CMC (low viscosity), 1% Polysorbate 20, in 0.9% NaCl. The microcarrier dose delivered was determined indirectly by weighing the residual dose in the injection vial and correcting for residual injection vehicle. The hGH dose was then computed from the protein loading of the microcarriers determined by nitrogen analysis.

Blood samples were collected at pre-determined intervals for up to 10 days after injection. Blood samples of 250 µl were collected during the first 24 hours and at least 400 µl at time points after 24 hours. Blood samples were clotted and hGH concentrations in serum were determined using a radio-immuno assay (RIA) using an RIA kit from ICN.

For the determination of pharmacokinetic parameters, hGH in saline was administered to rats by subcutaneous bolus injection, intravenously or delivered via an osmotic pump which was implanted subcutaneously.

Three groups of rats received single subcutaneous injections of hGH in 0.9% NaCl at 0.5 or 7.5 mg/kg at a dose volume of 1.0 ml/kg and two groups received single intravenous bolus injections of hGH in 0.9% NaCl solution at about 1.0 mg and 5.0 mg of hGH per kg rat with a dose volume of 1.0 ml/kg. For the Alzet® pump study, rats were divided into four groups of three rats each, randomized by body weight and dosed with about 20 mg/ml and 40 mg/ml hGH in 0.9% saline solution loaded into pumps (Alzet® Model 2002, 200 µl, 14 days release), and with about 4 mg/ml and 12 mg/ml hGH in 0.9% saline solution loaded into pumps (Alzet Model 2ML4, 2ml, 28 days release). Expected release rates from the pumps correspond to about 2% and 4 to 6% of the ProLease hGH dose (about 15 mg/kg) per day, respectively. The Alzet pumps were implanted subcutaneously in the inter-scapular region after soaking for 1–2 minutes in sterile saline.

The formulations of hGH sustained release microcarriers, synthesized as described in Example 5 contained 15% w/w hGH complexed with Zn in a ratio of 6:1 Zn:hGH; 0%, 1%, 3% or 6% w/w zinc carbonate; and 8K unblocked PLGA, 10K blocked PLGA or 31K unblocked PLGA.

To evaluate the various hGH sustained release formulations, Cmax, Cd5 and Cmax/Cd5 were the in vivo indices used, where Cmax is the maximum serum concentration observed, and Cd5 is the serum concentration at day 5 which should approximate the steady state concentration. The results were as follows:

| Formulation | 'Burst' in vitro (%) | % Monomer Day 7 | Cmax (ng/ml) | C day 5 (ng/ml) | Cmas/Css |
|---|---|---|---|---|---|
| 8K PLGA unblocked 0% ZnCO3 | 22.0 ± 0.9 | 99.3* | 323.3 ± 98.6 | 20.4 ± 14.2 | 19.5 ± 10.6 |
| 8K PLGA unblocked 1% ZnCO3 | 16.4 ± 1.6 | 97.3* | 309.0 ± 67.1 | 20.4 ± 14.2 | 39.5 ± 17.7 |
| 8K PLGA unblocked 3% ZnCO3 | 15.9 ± 6.9 | 98.7 | 670.5 ± 244.4 | 9.0 ± 4.2 | 44.8 ± 22.6 |
| 8K PLGA unblocked 6% ZnCO3 | 17.6 ± 2.7 | 99.3 | 358.0 ± 58.9 | 18.8 ± 14.7 | 42.4 ± 6.8 |
| 31K PLGA unblocked 0% ZnCO3 | 12.3 ± 1.1 | 98.2 | 592 ± 318.2 | 4.5 ± 1.5 | 132.5 ± 47.9 |
| 31K PLGA unblocked 1% ZnCO3 | 11.4 ± 1.3 | 98.8 | 432.7 ± 91.6 | 5.1 ± 0.3 | 84.1 ± 14.9 |
| 31K PLGA unblocked 3% ZnCO3 | 7.9 ± 1.9 | 99.4 | 643.6 ± 203.9 | 8.0 ± 2.6 | 93.3 ± 62.0 |
| 31K PLGA unblocked 6% ZnCO3 | 15.8 ± 0.5 | 99.8 | 1691.8 ± 340.0 | 6.6 ± 0.8 | 262.2 ± 83.5 |
| 10K PLGA unblocked 1% ZnCO3 | 12.7 ± 0.1 | 99.3 | 615.9 ± 384.3 | 4.5 ± 1.0 | 155.0 ± 126.8 |
| 10K PLGA blocked 3% ZnCO3 | 18.1 ± 3.2 | 99.6 | 1053.2 ± 293.3 | 3.6 ± 0.8 | 291.7 ± 71.1 |
| 10K PLGA blocked 6% ZnCO3 | 9.9 ± 1.4 | 99.0 | 1743.5 ± 428.4 | 4.9 ± 2.7 | 516.1 ± 361.6 |

*Value obtained from duplicate batch of the same formulation.

The results of the screening showed that the two unblocked (8K and 31K) polymers had different in vivo release kinetics compared to the original formulation, which used blocked 10K PLGA and 6% w/w zinc carbonate. Cmax values were generally lower with the unblocked polymer formulations than with the original formulation which suggested that the in vivo 'burst' may be lower with the unblocked polymer formulations. The 'burst' was defined as the percent of hGH released in the first 24 hours after injection. The in vitro 'burst' values were between 8–22%. The zinc carbonate content of the formulations did not appear to have an effect on the 'burst' or the in vitro release profile.

The serum concentrations between days 4 and 6 were maintained at a fairly constant level above baseline (or the pre-bleed levels) with the unblocked polymer formulations, while serum concentrations with the blocked formulations, at the same time points were close to the baseline levels. The in vitro release data for up to 7 days showed that the released hGH protein was monomeric. Useful data could not be obtained beyond day 6 because of anti-hGH antibody formation in the rats.

EXAMPLE 15

In Vivo Release of hGH from Aggregation-Stabilized hGH Microcarriers in Immunosuporessed Rats Two groups of male Sprague-Dawley rats (N=3) (control groups), weighing 400±50 g (S.D.) were injected as described in Example 14 with the microcarriers of Example 5. Two additional groups (N=3) of rats (test groups) were also given daily intraperitoneal injections of 10 mg cyclosporin A and 5 mg hydrocortisone in 0.5 ml sterilized saline for injection (USP) per kg of body weight for days 0 to 14 and then injections three times a week for days 15–28. No antibody titers were detected in these rats for the duration of treatment.

The control group did not receive injections to suppress their immune response to hGH. Antibodies were detected after day 6 in these rats.

Figure 13:
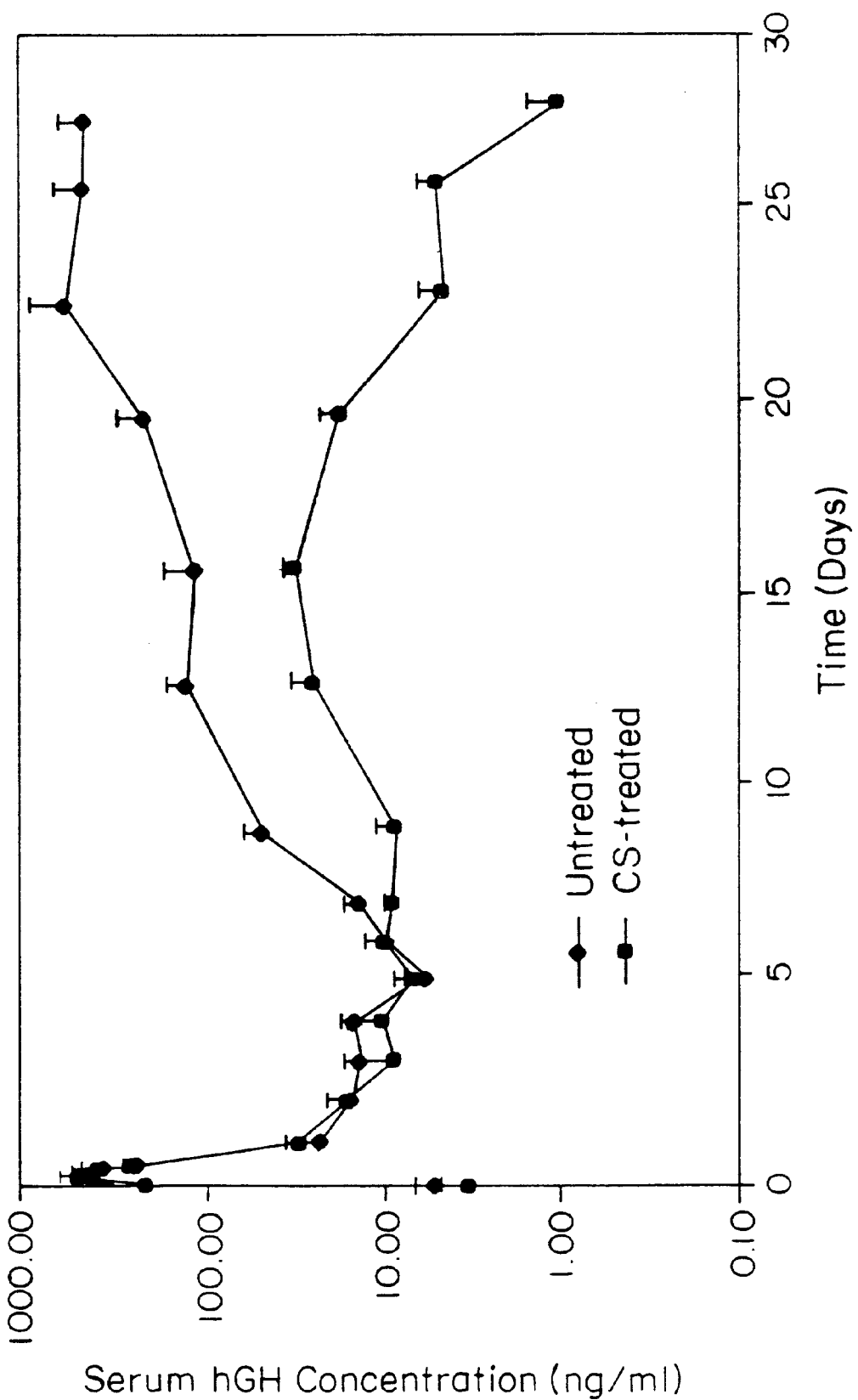
FIG. 13 is a plot of the serum concentration (ng/ml) of hGH versus time over a 28 day interval in rats which were subcutaneously administered a) aggregation-stabilized hGH microcarriers of 31K unblocked PLGA containing 1% $ZnCO_3$ of Example 5 wherein the rats were immunosuppressed with cyclosporin A and hydrocortisone and b) the same hGH microcarriers wherein the rats were not immunosuppressed.
Figure 14:
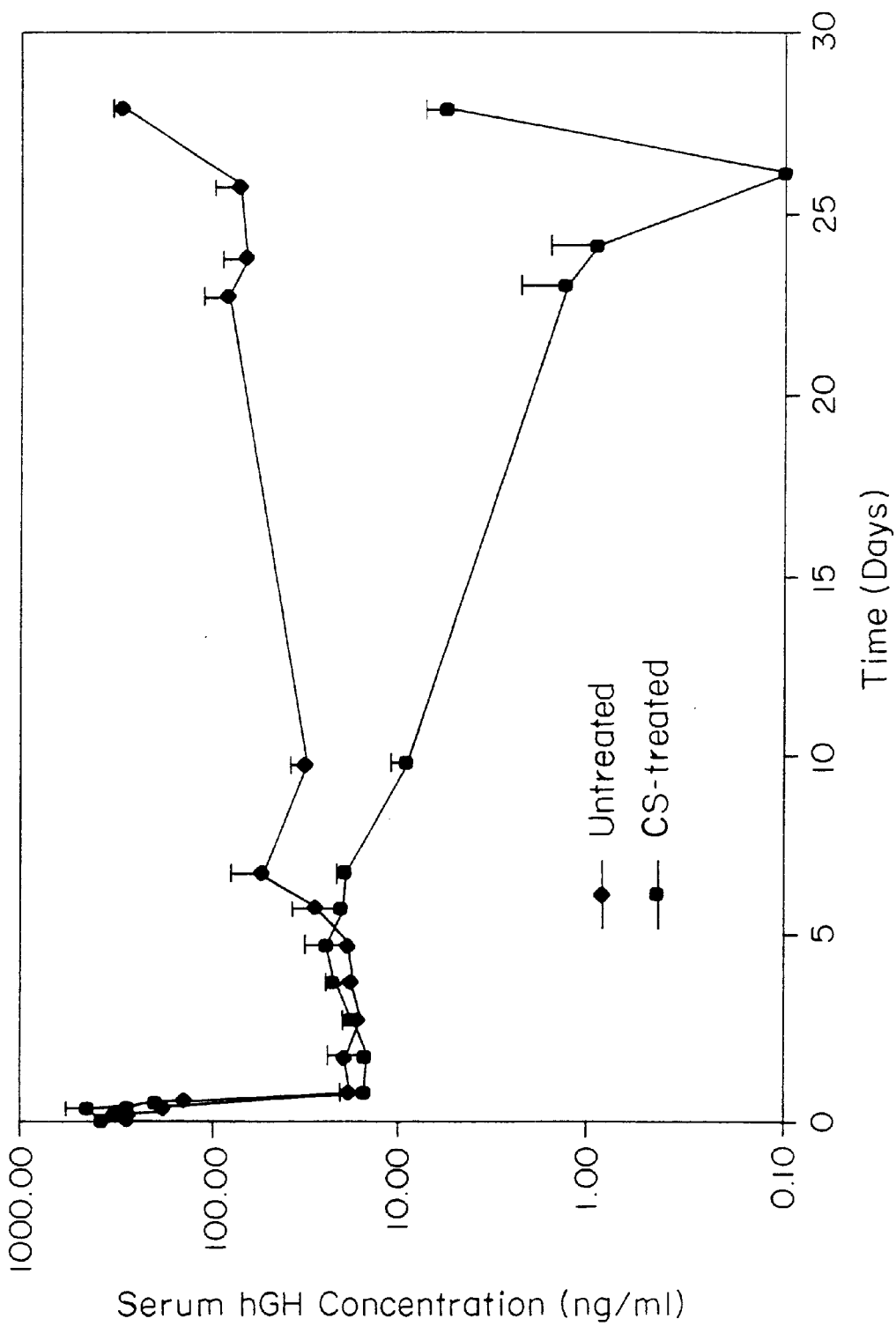
FIG. 14 is a plot of the serum concentration (ng/ml) of hGH versus time over a 28 day interval in rats which were subcutaneously administered a) aggregation-stabilized hGH microcarriers of 8K unblocked PLGA containing 1% $ZnCO_3$ of Example 5 wherein the rats were immunosuppressed with cyclosporin A and hydrocortisone and b) the same hGH microcarriers wherein the rats were not immunosuppressed.

The serum levels of hGH in the rats of the experimental groups and the control groups were determined by RIA through day 28. These results are provided in FIGS. 13 and 14. The results for both pairs of control and experimental groups were the same through day 6 suggesting that the cyclosporin A/hydrocortisone treatment did not affect the measured serum concentrations of hGH. The results further show that the control groups' serum levels of hGH were artificially high due to their production of antibodies to hGH.

The results for the experimental groups, in which antibody formation was suppressed, showed sustained release of hGH for up to 24 days and 26 days for the 31K unblocked PLGA and 8K blocked PLGA microcarriers, respectively, of Example 5.

EXAMPLE 16

In Vivo Release of hGH From Aggregation-Stabilized hGH Microcarriers in Rhesus Monkeys The objective of this primate study was to evaluate the pharmacokinetic profiles of different hGH sustained release formulations as compared to more traditional methods of administering hGH (e.g., bolus sc injections, daily sc injections and sc injection combined with the use of an osmotic pump) and to determine which hGH sustained release formulation gave the optimal hGH blood concentration profile.

The formulations for the hGH sustained release microcarriers tested were 1) 15% hGH (complexed with $Zn^{+2}$ at a 6:1 $Zn^{+2}$:hGH ratio), 6% w/w zinc carbonate and 10K blocked PLGA; 2) 15% hGH (complexed with $Zn^{+2}$ at a 6:1 $Zn^{+2}$:hGH ratio), 1% w/w zinc carbonate and 8K unblocked PLGA ("RG502H" PLGA polymer); and 3) 15% hGH (complexed with $Zn^{+2}$ at a 6:1 $Zn^{+2}$:hGH ratio), 1% w/w zinc carbonate and 31K unblocked PLGA ("RG503H" PLGA polymer). The microcarriers were formed as described in Example 5.

There were four monkeys per group and each animal received a single subcutaneous injection into the dorsal cervical region on Day 1. A dose of 160 mg of hGH sustained release microcarriers (24 mg of hGH) was administered to each monkey in 1.2 ml of injection vehicle through a 20 gauge needle. The injection vehicle was an aqueous vehicle containing 3% w/v low viscosity Carboxymethyl Cellulose (sodium salt), 1% v/v Tween 20 (Polysorbate 20) and 0.9% sodium chloride.

The hGH dose was intended to provide measurable hGH serum concentrations for pharmacokinetic analysis. To obtain pharmacokinetic parameters, additional study groups of four monkeys each were included, specifically 1) a single subcutaneous injection (24 mg hGH), 2) daily subcutaneous injections (24 mg/28 days=0.86 mg hGH/day), 3) a subcutaneous injection (3.6 mg hGH) combined with an Alzet osmotic pump (20.4 mg hGH)(total dose of 24 mg hGH), and 4) a subcutaneous injection of the injection vehicle as a control (only used 3 monkeys for the vehicle control group).

The osmotic pump gave sustained serum hGH levels comparable to the hGH microcarriers up to day 28 as programmed to release hGH. The pumps were removed on day 31.

Blood samples were collected at the following times for hGH and IGF-1 analyses: -7, -5, -3 days, pre-dose and, 0.5, 1, 2, 3, 5, 8, 10, 12, 24, 28, 32 and 48 hours, 5, 4, 6, 8, 11, 14, 17, 20, 23, 26, 29, 32, 25, 28, 41, 44, 47, 50, 53, 56 days post-dose.

The concentrations of IGF-1, which is expressed when a body has an effective serum level of hGH, and hGH in the serum were then measured. An IRMA kit from RADIM (distributed by: Wein Laboratories, P.O. Box 227, Succasunna, N.J.) was used to quantify hGH in monkey serum. The IRMA assay had a limit of quantification in PBS buffer of 0.1 ng/mL and in pooled juvenile rhesus monkey serum of 1.5 ng/mL with a basal GH level of about 4 ng/mL. RIA was used to quantify the IGF-1 serum levels.

Figure 15:
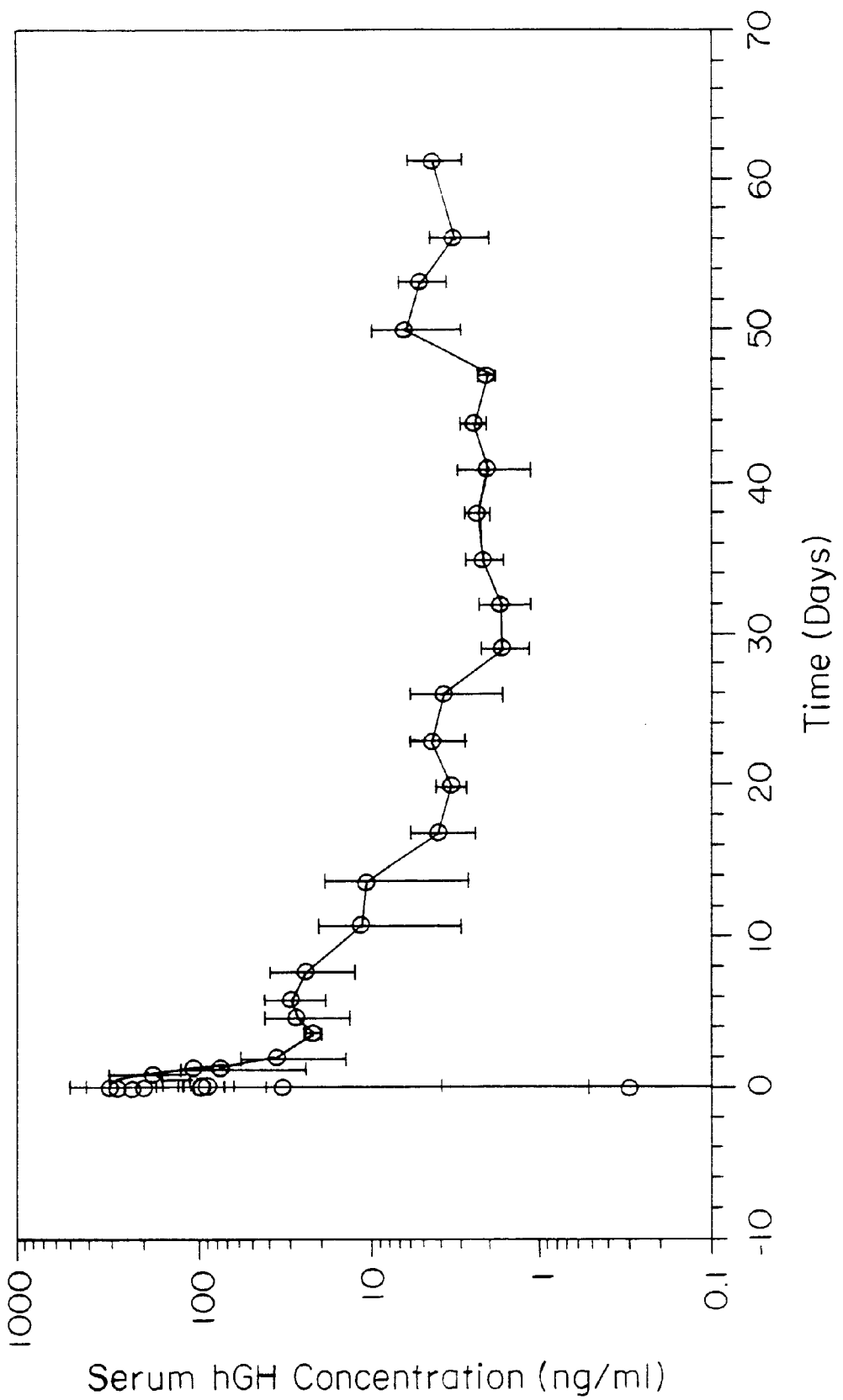
FIG. 15 is a plot of the serum concentration (ng/ml) of hGH versus time for a 61 day interval in monkeys which were subcutaneously administered aggregation-stabilized hGH microcarriers of Example 5 containing 15% hGH (complexed with $Zn^{+2}$ at a 6:1 $Zn^{+2}$:hGH molar ratio), 6% w/w $ZnCO_3$ and 10K blocked PLGA.
Figure 16:
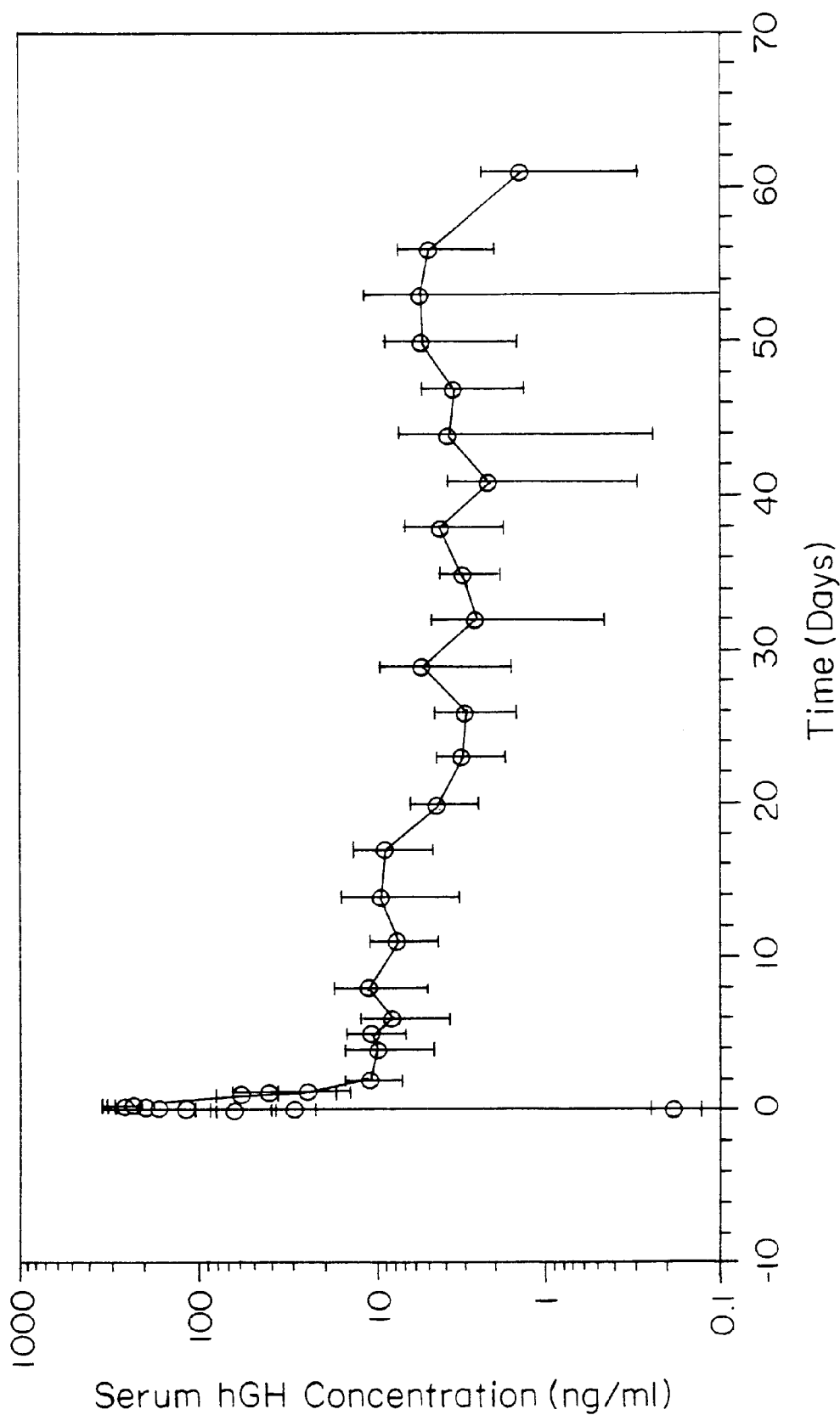
FIG. 16 is a plot of the serum concentration (ng/ml) of hGH versus time for a 60 day interval in monkeys which were subcutaneously administered aggregation-stabilized hGH microcarriers of Example 5 containing 15% hGH (complexed with $Zn^{+2}$ at a 6:1 $Zn^{+2}$:hGH molar ratio), 1% w/w $ZnCO_3$ and 8K unblocked PLGA.
Figure 17:
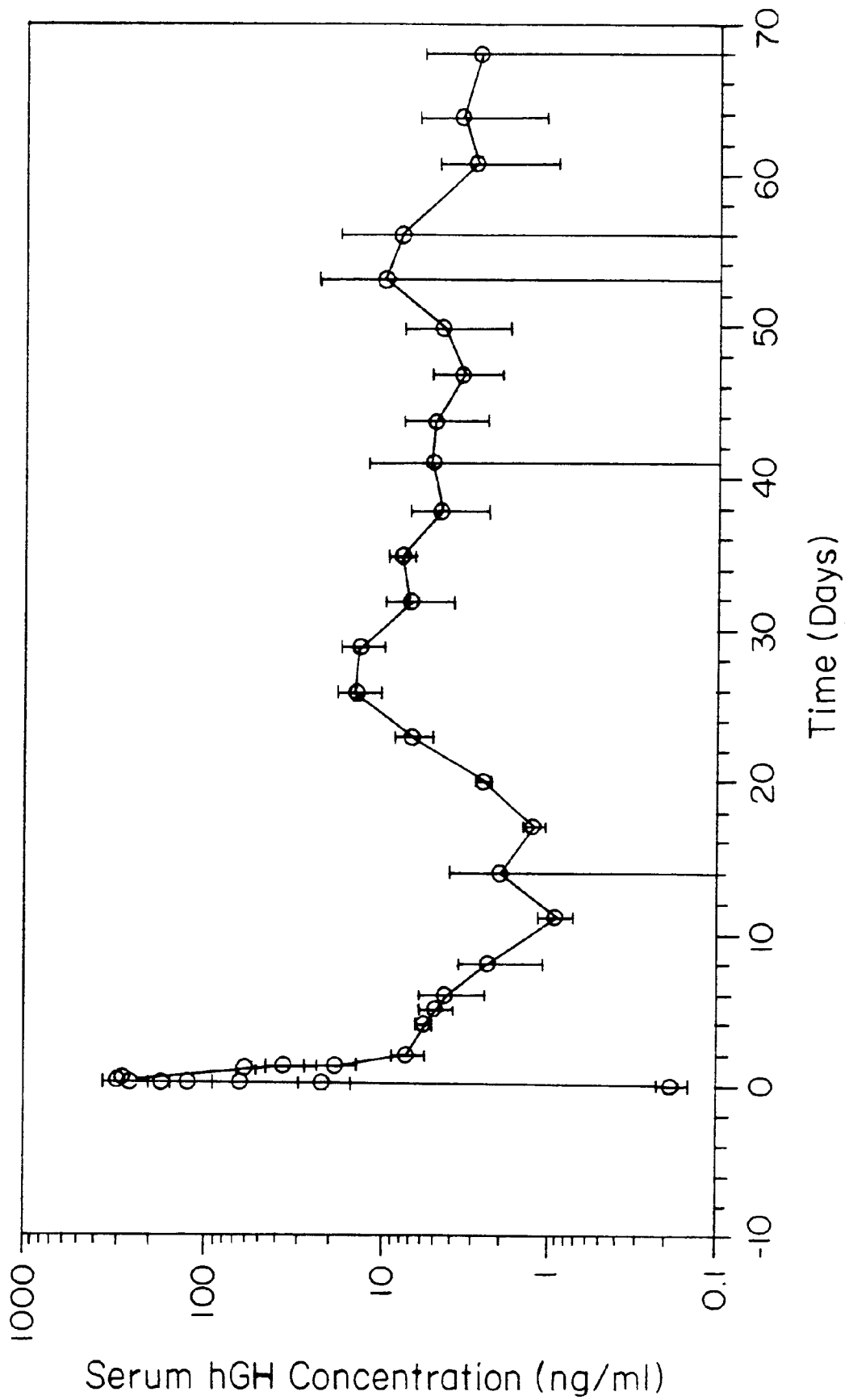
FIG. 17 is a plot of the serum concentration (ng/ml) of hGH versus time for a 68 day interval in monkeys which were subcutaneously administered aggregation-stabilized hGH microcarriers of Example 5 containing 15% hGH (complexed with $Zn^{+2}$ at a 6:1 $Zn^{+2}$:hGH molar ratio), 1% w/w $ZnCO_3$ and 31K unblocked PLGA.
Figure 18:
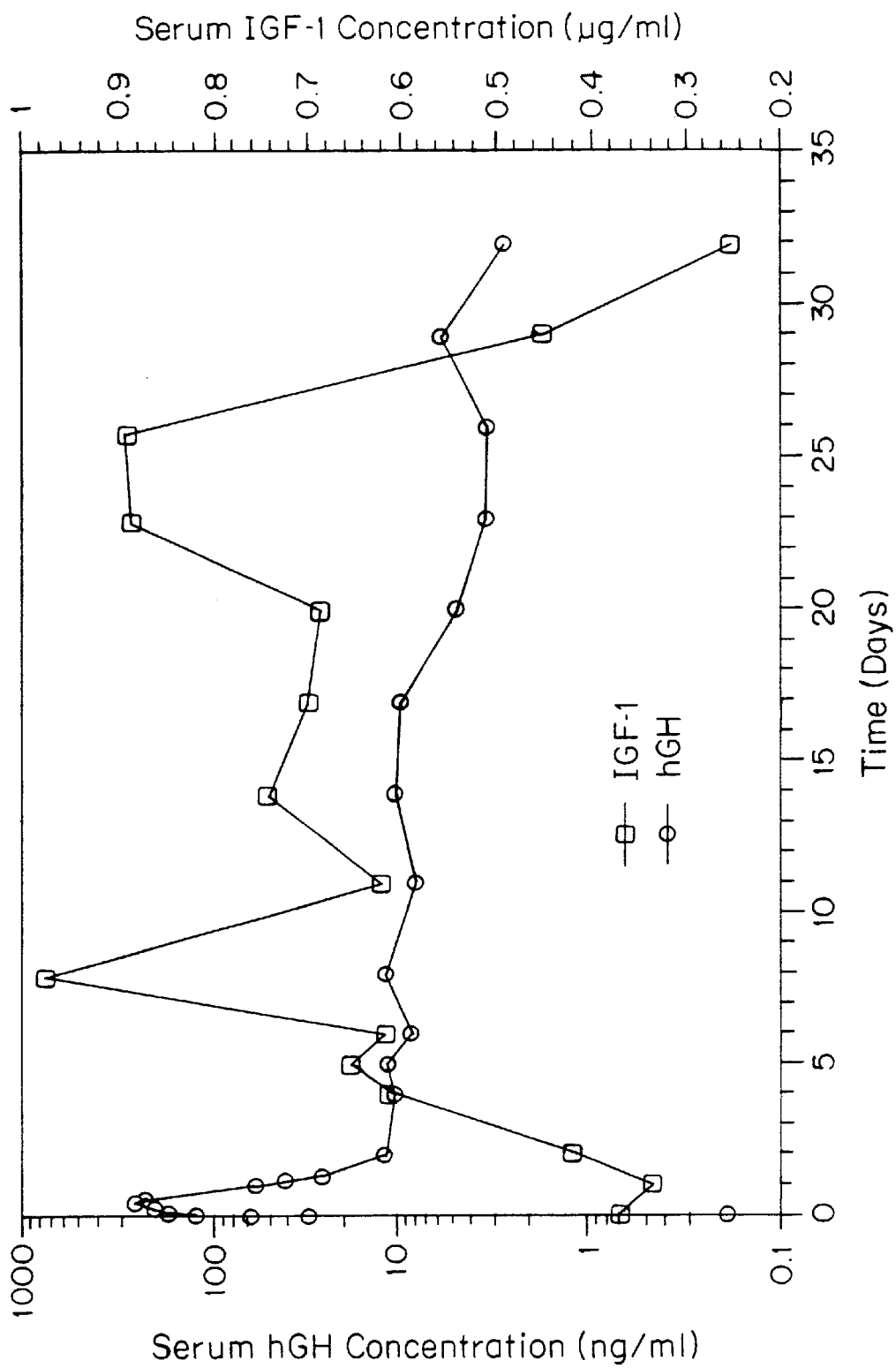
FIG. 18 is a plot of the serum concentration (ng/ml) of hGH and IGF-1 versus time for a 32 day interval in monkeys which were subcutaneously administered aggregation-stabilized hGH microcarriers of Example 16 in 8K unblocked PLGA.

The results of the hGH serum level assays for the 10K blocked PLGA, 8K unblocked PLGA and 31K unblocked hGH microcarriers of Example 5 are provided in FIGS. 15–17, respectively. Further, the results of the hGH and IGF-1 serum assays for the 8K unblocked PLGA microcarriers of Example 5 are shown in FIG. 18.

Figure 19:
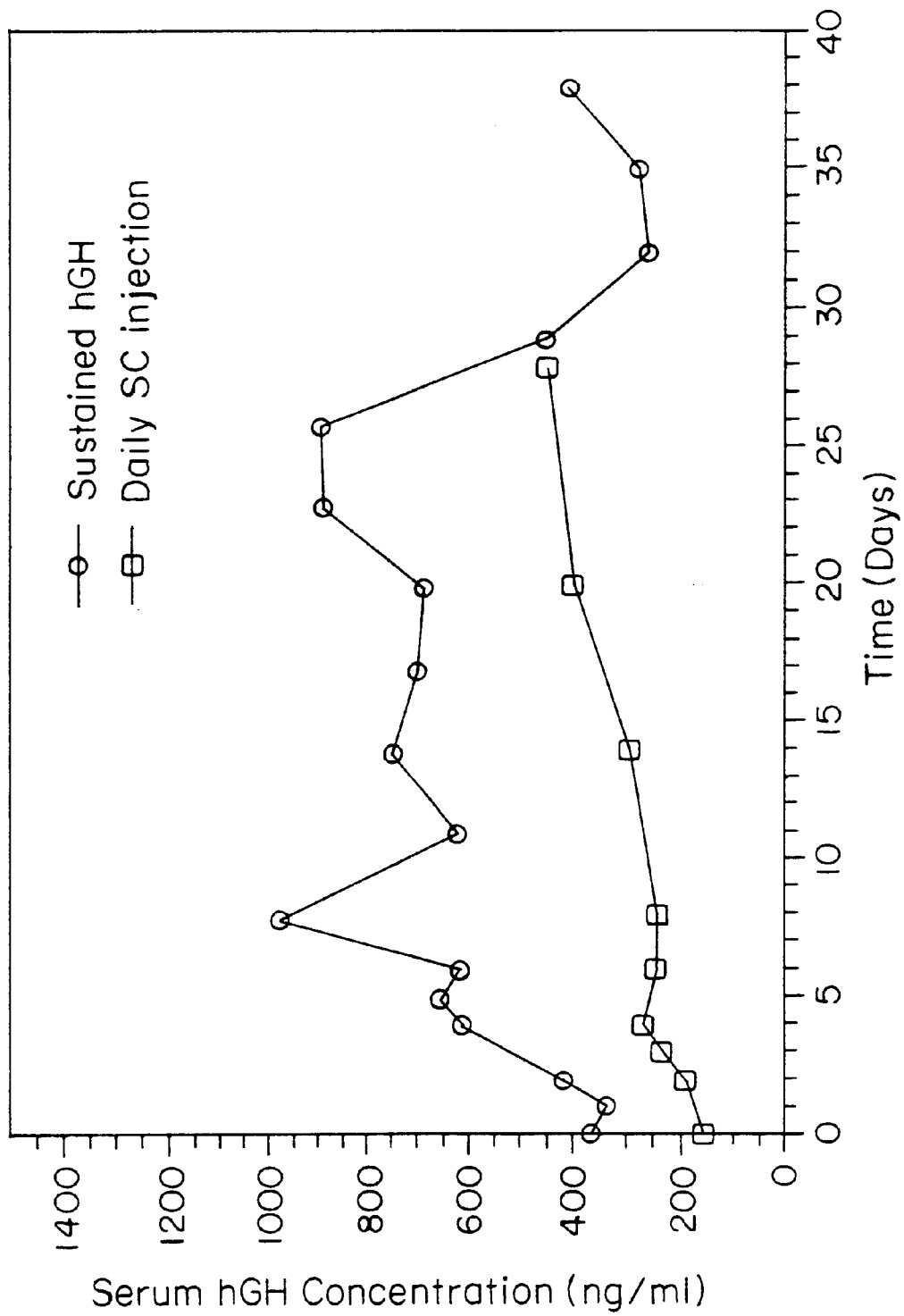
FIG. 19 is a plot of the serum concentration (ng/ml) of hGH versus time for 30 and 39 day intervals for a) aggregation-stabilized hGH 8K unblocked PLGA microcarriers and b) daily aqueous hGH injections, respectively.

In addition, a comparison of the results of the IGF-1 serum assays for the 8K unblocked PLGA microcarriers of Example 5 as compared to the serum levels for daily subcutaneous injections of hGH are shown in FIG. 19.

The results showed that the hGH sustained release microcarriers were releasing significant, sustained levels of hGH over a one month period while the subcutaneous injections were not able to maintain the same serum levels.

The IGF-1 serum profile showed that serum IGF-1 concentrations were elevated above the baseline values between days 2 and 29 after administering the microparticles. This shows that enough hGH was being released from the hGH sustained release microcarriers to cause a pharmacodynamic effect. This also indicates that the hGH released was biologically active which suggests that the encapsulation process had not adversely affected the biopotency of hGH.

EXAMPLE 17

In Vivo Release of Aggregation-Stabilized EPO from Polymeric Microcarriers in Immunosuppressed Rats Male Sprague-Dawley rats, weighing 400±50 g (S.D.), were used as the animal model. The rats were not fasted before the experiments and subsequently were fed with a standard diet, an iron supplement, and allowed free access to water. Iron dextran (Sigma Co., St. Louis, Mo.) 5 mg/kg was injected intraperitoneally twice a week.

These experiments utilized the immunosuppression method described in Examples 11 and 15 for suppressing antibody production in the test animals in response to the EPO released (or injected) to obtain accurate profiles of serum EPO levels.

The purpose of the first experiment was to compare the in vivo pharmacodynamic effects of aggregation-stabilized EPO released from sustained release microcarriers to EPO injected subcutaneously as a bolus, specifically upon serum reticulocyte profiles. Two groups of three rats were injected subcutaneously in the interscapular region on day 0 with 10,000 units of RMAm7 EPO microcarriers (unblocked 10K PLGA containing 10% $MgCO_3$ and 5% Am7) and subsequently on day 28 with a 2,000 unit bolus of aqueous EPO. The control group did not receive the cyclosporin A/hydrocortisone therapy, which the test group did receive.

Blood samples were taken from the tail vein of each rat at 1, 3, 4, 8, 10, 14 16, 20, 24, 28, 30 or 31, 32 and 36 hours after injection. Additional blood samples were then taken approximately twice a week for the following 5 weeks.

Figure 20:
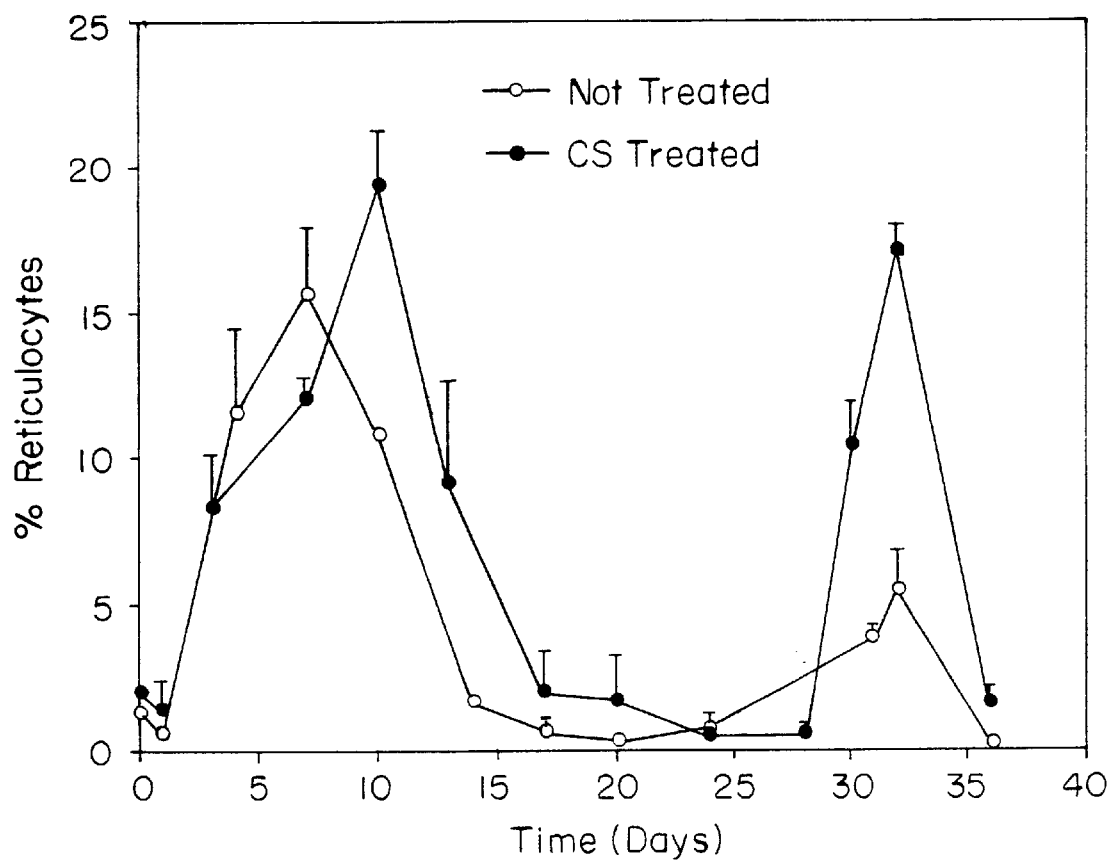
FIG. 20 is a plot of the percent reticulocytes in blood of cyclosporin/hydrocortisone (CS/HC) treated and untreated rats, which were subcutaneously injected with 10,000 units of the EPO sustained release microcarriers RMAm7, described in Example 17 a bolus of 2,000 units of aqueous EPO, administered on day 28, respectively, versus time over a 36 day interval.

Blood reticulocyte levels were counted for selected blood sample. The results are provided in FIG. 20. FIG. 20 shows higher reticulocyte counts in immunosuppressed rats in response to both the aggregation-stabilized EPO microcarriers and the EPO bolus. The non-immunosuppressed rats (control group) showed lower reticulocyte levels due to antibody formation resulting from the immune systems' responses to EPO. This is particularly shown by the lack of a significant increase in reticulocyte levels in the control group after receiving the EPO bolus on day 28.

FIG. 20 also shows that injection with sustained release microcarriers resulted in a longer period of elevated serum reticulocyte levels than did a bolus of EPO.

The purpose of the second experiment was to compare the in vivo pharmacokinetic and pharmacodynamic effects of EPO released from various sustained release microcarriers.

The rats in each of four groups rats (N=3) were injected subcutaneously in the interscapular region with one of four of the following formulations of microcarriers:

RMAm1 Unblocked 10K PLGA/10% $MgCO_3$/5% Am1
RMMa1 Unblocked 10K PLGA 10% $MgCO_3$/5% Mal
PZZn1 Blocked 10K PLGA/10% $ZnCO_3$/5% Zn1
RMAm7 Unblocked 10K PLGA/10% $MgCO_3$/5% Am7

Each rat received between 10,000 to 12,000 units per animal. Each rat was also given daily an intraperitoneal injection of 10 mg of cyclosporin A and 5 mg of hydrocortisone.

Blood samples were taken from the tail vein of each rat at 1, 2, 4, 8, 10 (optionally), 24, 36 and 48 hours after injection. Additional blood samples were then taken approximately once a day for the following 10 days and approximately two times per week for the next two weeks. The EPO concentration in the rat serum samples was determined using by ELISA. In addition, blood reticulocyte levels were counted.

Figure 21:
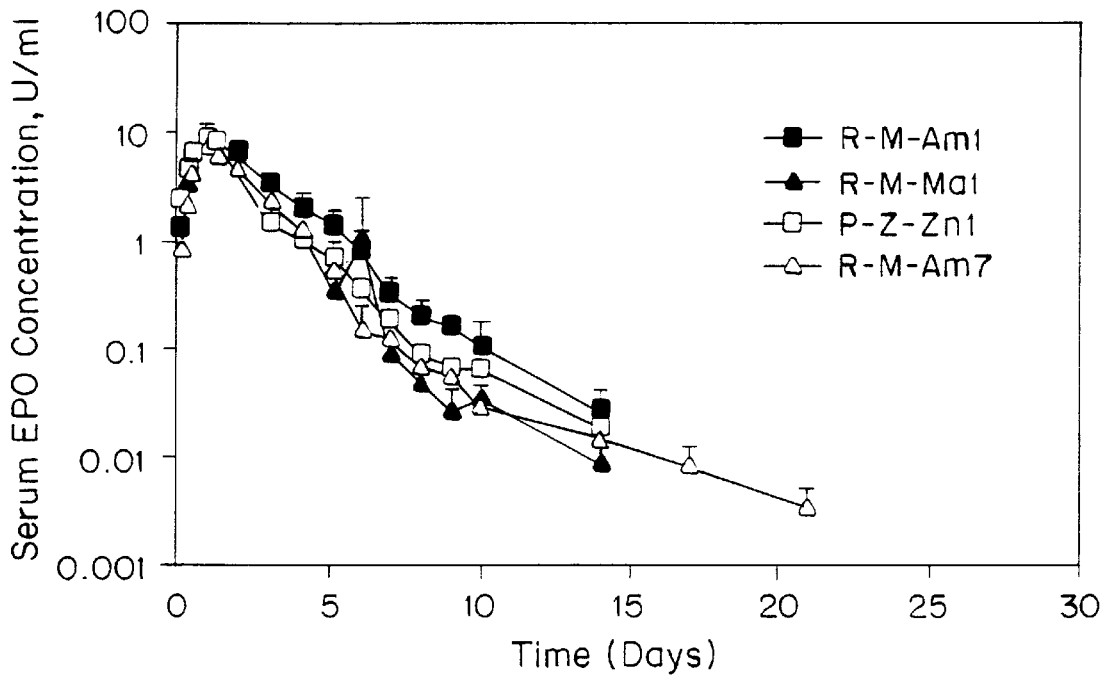
FIG. 21 is a plot of the serum concentration (IU/ml) of EPO in rats, which were subcutaneously administered various EPO sustained release microcarriers, described in Example 6, versus time over a 22 day interval.
Figure 22:
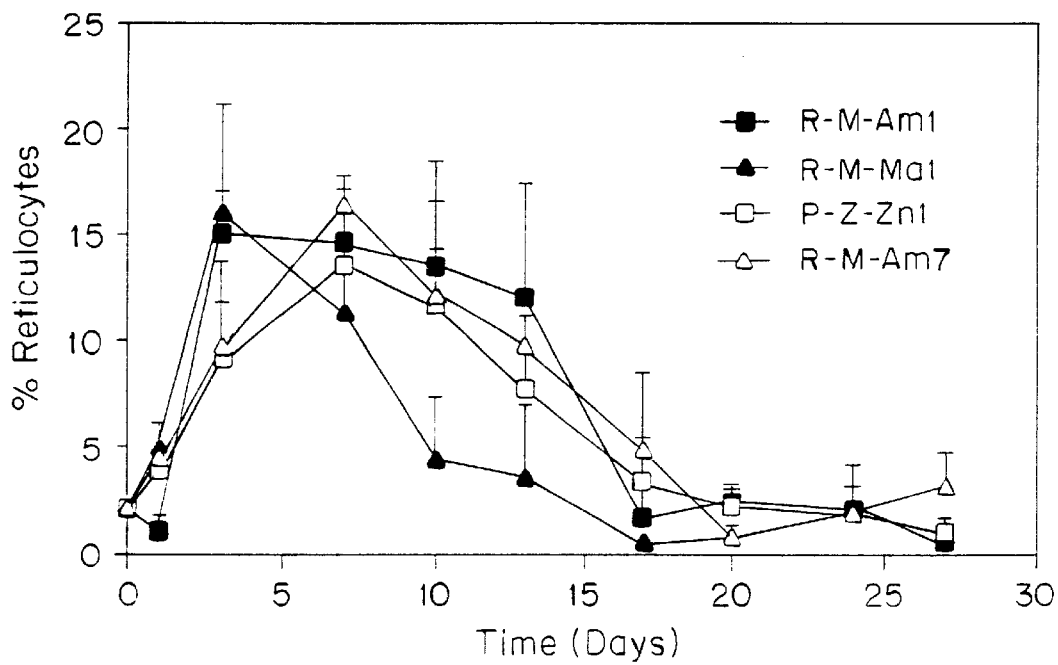
FIG. 22 is a plot of the percent reticulocytes in blood of rats, which were subcutaneously injected with 10,000 units of various EPO sustained release microcarriers, described in Example 6, versus time over a 28 day interval.

Serum EPO and blood reticulocyte profiles for these formulations are provided in FIGS. 21 and 22. EPO levels remained above baseline in these animals for approximately 14 days, showing a sustained release of biologically active EPO. Elevated reticulocyte levels were observed for about 17 days. Further, the response of immature and total reticulocyte levels were proportional and not significantly different from each other following EPO treatment.

EXAMPLE 18

Effect of Zinc Carbonate on Release Levels of Aggregation-Stabilized IFN-α,2b in Rats Rats (N=4) in three test groups were injected, as described in Example 9, with the microcarriers of formulas 4 and 6–8 of Example 2. The dose of IFN for each rat was about 0.8 mg/kg.

The purpose of the test was to determine if the initial burst and sustained level of IFN-α,2b released in vivo can be varied by changing the weight ratio of zinc carbonate to IFN-α,2b in microcarriers.

The weight ratio of zinc carbonate to IFN in microcarriers tested for initial burst effects were 0:1, 1:1, 3:1 and 8:1. Blood samples were then taken from the tail vein of each rat at 1, 2, 4, 8, 12, 24, 32, 48, 72, 96, 120, 144 and 168 hours after injection. The IFN-α,2b concentrations in the rat serum samples were determined by IRMA. The tests found that the addition of zinc carbonate to the formulation reduces initial burst in vivo. Specifically, initial bursts measured, as a percentage of the total IFN in the microcarriers which were released over the first 24 hours, for microcarriers having weight ratios of 0:1, 1:1, 3:1 and 8:1 were 35±13%, 23±7%, 13±5% and 8±1%, respectively.

These initial burst results suggest that the amount of metal cation in the polymer can be used to vary the burst.

Figure 23:
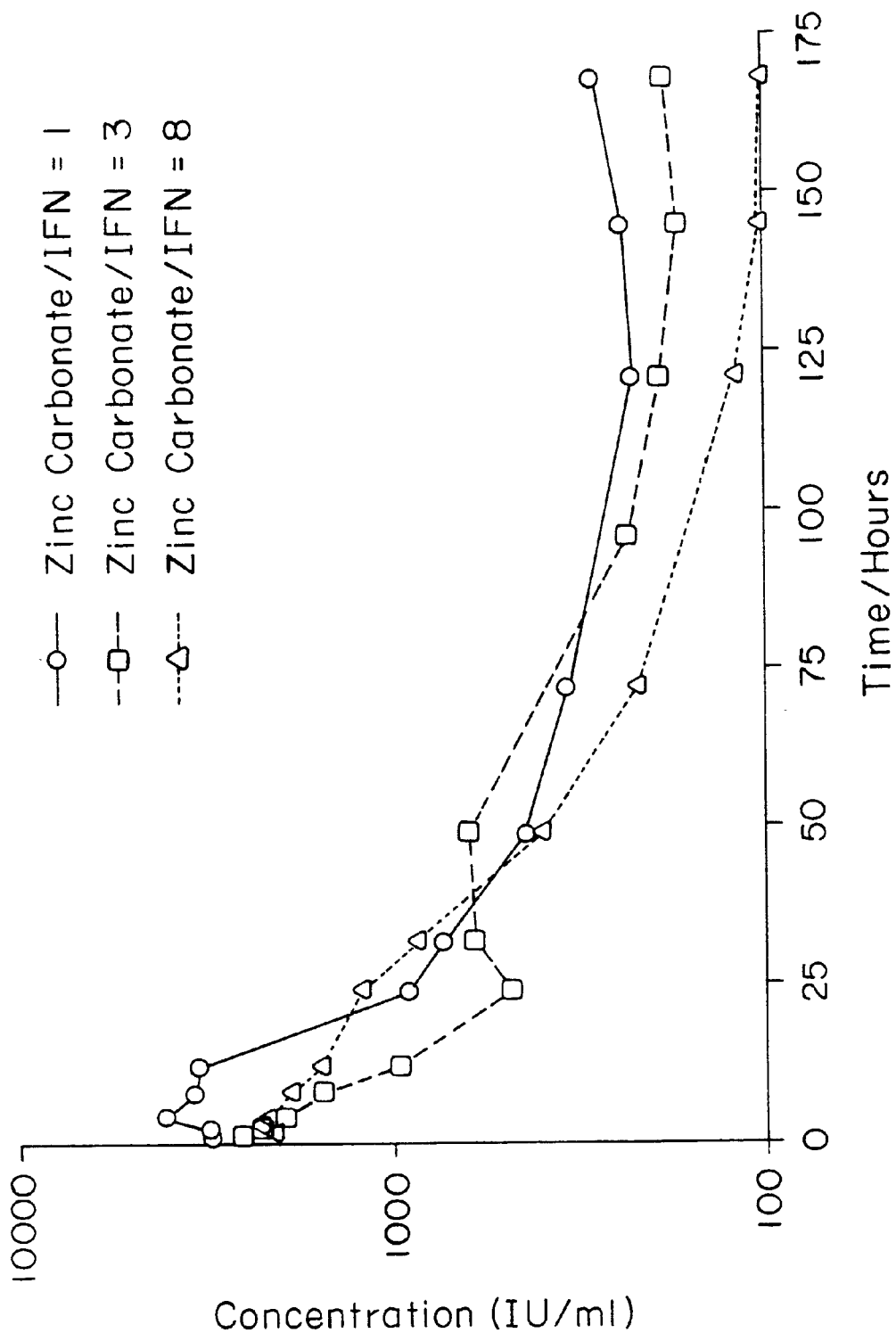
FIG. 23 is a plot of the serum concentration (IU/ml) of IFN-α,2b versus time over a 7 day interval in rats which were subcutaneously administered three different IFN-α,2b controlled release microcarriers of Example 2 having zinc carbonate to IFN-α,2b ratios of 1:1, 3:1 and 8:1.

For the sustained release test, the weight ratio of zinc carbonate to IFN in microcarriers tested were 1:1, 3:1 and 8:1. The sustained release results of this test are presented in FIG. 23. The sustained level observed for Formula 7 of Example 1, having a weight ratio of 1:1, was 250±30 IU/ml during days 5–7. The level observed for Formula 6, having a weight ratio of 3:1, was 180±10 IU/ml during days 5–7, whereas that for a Formula 8, having a weight ratio of 8:1, was 110±10 IU/ml.

Equivalents

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A sustained release device of a water soluble, biologically active protein or peptide wherein said protein or peptide is susceptible to aggregation, comprising:

a) a biocompatible polymeric matrix; and
b) particles of aggregation-stabilized, biologically active protein or peptide which include a biologically active protein or peptide and an aggregation stabilizer, wherein the aggregation-stabilizer is a multivalent metal cation from a metal cation component selected from the group consisting of metal salts, metal hydroxides and basic salts of weak acids having a metal cation, the biologically active protein or peptide and the metal cation are complexed and said particles are disposed within the biocompatible polymeric matrix.

2. A sustained release composition of claim 1 wherein the metal cation is a biocompatible multivalent cation selected from the group consisting of $Zn^{+2}$, $Ca^{+2}$, $Cu^{+2}$, $Mg^{+2}$ and combinations thereof.

3. A sustained release composition of claim 1 further comprising a second metal cation component, wherein the second metal cation component is dispersed within the biocompatible polymeric matrix.

4. A sustained release composition of claim 3 wherein the second metal cation component is selected from the group consisting of magnesium hydroxide, magnesium carbonate, calcium carbonate, zinc carbonate, magnesium acetate, zinc acetate, magnesium sulfate, zinc sulfate, magnesium chloride, zinc chloride, zinc citrate, magnesium citrate and combinations thereof.

5. A sustained release composition of claim 1 wherein the biocompatible polymeric matrix comprises poly(lactide-co-glycolide).

6. The sustained release device of claim 1 wherein the molar ratio of metal cation component to biologically active protein or peptide is from about 1:2 to about 100:1.

7. The sustained release device of claim 6 wherein the molar ratio of metal cation component to biologically active protein or peptide is from about 2:1 to about 10:1.

8. A sustained release device of a water soluble, biologically active protein or peptide wherein said protein or peptide is susceptible to aggregation, comprising:
  a) a biodegradable polymeric matrix; and
  b) particles of aggregation-stabilized, biologically active protein or peptide which include a biologically active protein or peptide and an aggregation stabilizer wherein the aggregation-stabilizer is a multivalent metal cation from a metal cation component selected from the group consisting of metal salts, metal hydroxides and basic salts of weak acids having a metal cation, the biologically active protein or peptide and the metal cation are complexed and said particles are disposed within the biodegradable polymeric matrix.

* * * * *